(12) United States Patent
Hirano et al.

(10) Patent No.: US 10,066,249 B2
(45) Date of Patent: Sep. 4, 2018

(54) METHOD FOR PRODUCING ACETYLATED SPHINGOID BASE

(71) Applicant: Kao Corporation, Chuo-ku, Tokyo (JP)

(72) Inventors: Kumiko Hirano, Tokyo (JP); Atsuko Hayase, Tochigi (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 15/035,622

(22) PCT Filed: Nov. 20, 2014

(86) PCT No.: PCT/JP2014/081486
§ 371 (c)(1),
(2) Date: May 10, 2016

(87) PCT Pub. No.: WO2015/076423
PCT Pub. Date: May 28, 2015

(65) Prior Publication Data
US 2016/0298150 A1     Oct. 13, 2016

(30) Foreign Application Priority Data
Nov. 21, 2013 (JP) ................................. 2013-241166

(51) Int. Cl.
*C12P 13/02* (2006.01)
*C12P 13/00* (2006.01)
(Continued)

(52) U.S. Cl.
CPC ............... *C12P 13/02* (2013.01); *C12N 1/14* (2013.01); *C12N 9/1029* (2013.01); *C12N 15/80* (2013.01);
(Continued)

(58) Field of Classification Search
None
See application file for complete search history.

(56) References Cited

U.S. PATENT DOCUMENTS 5,578,641 A     11/1996   Jackson et al.
5,627,056 A  *  5/1997    Casey .................. A61K 8/68
                                                          424/401
(Continued)

FOREIGN PATENT DOCUMENTS

DE    10 2012 007 491 A1    10/2013
JP         2009-207493 A     9/2009
(Continued)

OTHER PUBLICATIONS

Guo et al., "Protein tolerance to random amino acid change", Proceedings of the National Academy of Sciences USA, vol. 101, No. 25, pp. 9205-9210, 2004.*

(Continued)

*Primary Examiner* — Richard C Ekstrom
(74) *Attorney, Agent, or Firm* — Sterne, Kessler, Goldstein & Fox P.L.L.C.

(57) ABSTRACT

Provided is a means for producing an acetylated sphingoid base using modified microorganism in the genus *Starmerella*, particularly *Starmerella bombicola*. A method for producing an acetylated sphingoid base comprising culturing a microorganism in the genus *Starmerella* to which a xenogeneic gene encoding a polypeptide having an activity to acetylate a sphingoid base is introduced.

22 Claims, 1 Drawing Sheet
Specification includes a Sequence Listing.

(a)

(b)

(51) Int. Cl.
| | | |
|---|---|---|
| C12N 1/14 | (2006.01) | |
| C12N 9/10 | (2006.01) | |
| C12N 15/81 | (2006.01) | |
| C12N 15/80 | (2006.01) | |

(52) U.S. Cl.
CPC ............ *C12N 15/815* (2013.01); *C12P 13/00* (2013.01); *C12P 13/001* (2013.01); *C12Y 203/01* (2013.01)

(56) References Cited

U.S. PATENT DOCUMENTS

| | | | |
|---|---|---|---|
| 2008/0299625 A1* | 12/2008 | Van Den Berg | C12P 13/02 435/128 |
| 2013/0035403 A1 | 2/2013 | Schaffer et al. | |
| 2015/0118721 A1 | 4/2015 | Schaffer et al. | |

FOREIGN PATENT DOCUMENTS

| | | |
|---|---|---|
| JP | 2013-511266 A | 4/2013 |
| WO | WO 95/12683 A1 | 5/1995 |
| WO | WO 2012/080116 A1 | 6/2012 |
| WO | WO 2013/152913 A1 | 10/2013 |

OTHER PUBLICATIONS

UniProtKB/Swiss-Prot Accession No. P53304.1, published Oct. 31, 2012.*

NCBI Reference Sequence XP_002493741.1, published Jul. 22, 2009.*

International Search Report (ISR) for PCT/JP2014/081486; I.A. fd Nov. 20, 2014, dated May 13, 2015, from the European Patent Office, Rijswijk, Netherlands.

International Preliminary Report on Patentability (IPRP), Chapter I of the Patent Cooperation Treaty, including the Written Opinion for PCT/JP2014/081486; I.A. fd Nov. 20, 2014, dated May 24, 2016, by the International Bureau of WIPO, Geneva, Switzerland.

Bibel, DJ et al.,"Antimicrobial activity of sphingosines," J Invest Dermatol. Mar. 1992;98(3):269-73, Elsevier, New York.

Bibel, DJ et al., "Topical sphingolipids in antisepsis and antifungal therapy," Clin Exp Dermatol. Sep. 1995;20(5):395-400, Blackwell Scientific Publications, Oxford.

Park, C. et al., "Cosmeceutical uses of new sphingolipids from yeast," Fragrance Journal 10:84-89 (1999), Fureguransujanaru Co. Inc., Japan.

Masukawa, Y. et al., "Characterization of overall ceramide species in human *stratum corneum*," J Lipid Res. Jul. 2008;49(7):1466-76. doi: 10.1194/jlr.M800014-JLR200. Epub Mar. 23, 2008, Am Soc for Biochem Molec Biol, Bethesda, MD.

Ichikawa, J. et al., "Changes in the ceramide profile of atopic dermatitis patients," J Invest Dermatol. Oct. 2010;130(10):2511-4. doi: 10.1038/jid.2010.161. Epub Jun. 24, 2010, Elsevier, New York.

ter Veld, F. et al, "Production of tetraacetyl phytosphingosine (TAPS) in *Wickerhamomyces ciferrii* is catalyzed by acetyltransferases Sli1p and Atf2p," Appl Microbiol Biotechnol. Oct. 2013;97(19):8537-46. doi: 10.1007/s00253-012-4670-3. Epub Jan. 15, 2013, Springer International, Berlin, Germany.

Barenholz, Y. et al., "Identification of the enzymatic lesions responsible for the accumulation of acetylated sphingosine bases in the yeast *Hansenula ciferri*," Biochim Biophys Acta. May 24, 1973;306(2):341-5, Elsevier Pub. Co., Amsterdam, Netherlands.

Rau, U et al., " Influence of substrate supply on the production of sophorose lipids by *Candida bombicola* ATCC 22214," Biotechnology Letters, Feb. 1996, vol. 18, Issue 2, pp. 149-154, Kluwer Academic Publishers.

Saerens, KMJ et al., "One-step production of unacetylated sophorolipids by an acetyltransferase negative *Candida bombicola*," Biotechnol Bioeng. Dec. 2011;108(12):2923-31. doi: 10.1002/bit.23248. Epub Jul. 12, 2011, Wiley, Hoboken, NJ.

Momoi, M. et al., "SLI1 (YGR212W) is a major gene conferring resistance to the sphingolipid biosynthesis inhibitor ISP-1, and encodes an ISP-1 N-acetyltransferase in yeast," Biochem J. Jul. 1, 2004;381(Pt 1):321-8, Portland Press, London, UK.

\* cited by examiner

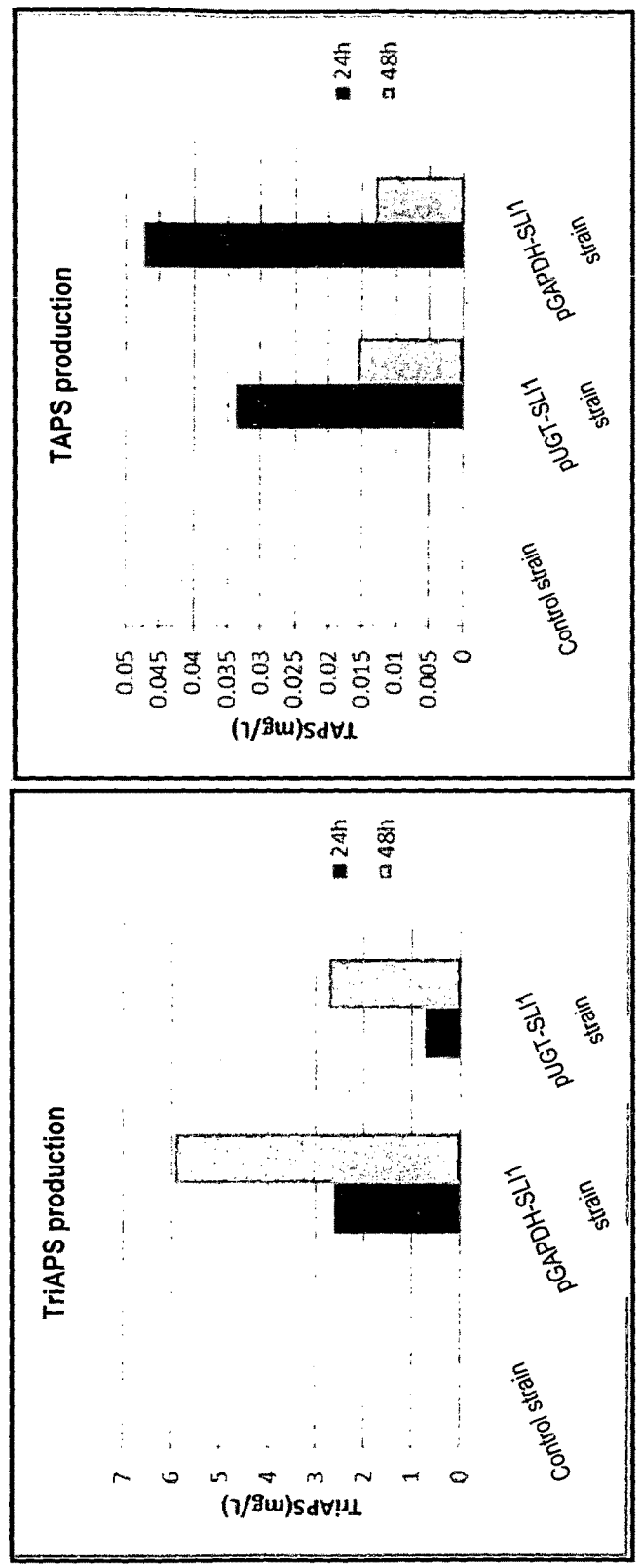

```
                        SEQUENCE LISTING

<160> NUMBER OF SEQ ID NOS: 47

<210> SEQ ID NO 1
<211> LENGTH: 1326
<212> TYPE: DNA
<213> ORGANISM: Wickerhamomyces ciferrii
<220> FEATURE:
<221> NAME/KEY: CDS
<222> LOCATION: (1)..(1326)

<400> SEQUENCE: 1 atg gtg gct gga cca aac aaa gat ctt gaa aac ctg gaa cgt atg atg     48
Met Val Ala Gly Pro Asn Lys Asp Leu Glu Asn Leu Glu Arg Met Met
1               5                  10                  15 tac tgg aag acc act ttg aaa gct tgg tca tgt ttc ctt gtt ggt gct     96
Tyr Trp Lys Thr Thr Leu Lys Ala Trp Ser Cys Phe Leu Val Gly Ala
                20                  25                  30 aaa tta aac gaa aaa tta gaa aca gat gat att tta aaa ggt atc cac    144
Lys Leu Asn Glu Lys Leu Glu Thr Asp Asp Ile Leu Lys Gly Ile His
            35                  40                  45 aaa tta ttc acg ttg agg gtt cag tta cgt ttg aat gtt ttc caa tat    192
Lys Leu Phe Thr Leu Arg Val Gln Leu Arg Leu Asn Val Phe Gln Tyr
        50                  55                  60 cct aaa aaa agg ttt gtt acc gaa gag ata aat ggt tgg tct gat gat    240
Pro Lys Lys Arg Phe Val Thr Glu Glu Ile Asn Gly Trp Ser Asp Asp
65                  70                  75                  80 ttt gtt gat ttt gtc gat tat cca act gat gat ttt gat att att gaa    288
Phe Val Asp Phe Val Asp Tyr Pro Thr Asp Asp Phe Asp Ile Ile Glu
                85                  90                  95 gct ttt aaa caa caa cat aat caa tat ttt gaa ttg ggt gtt caa aag    336
Ala Phe Lys Gln Gln His Asn Gln Tyr Phe Glu Leu Gly Val Gln Lys
                100                 105                 110 cct tta tgg aaa ttg gtt gta ttg aac cat caa tat tta gtt att ctt    384
```

```
            Pro Leu Trp Lys Leu Val Val Leu Asn His Gln Tyr Leu Val Ile Leu
                        115                 120                 125 tgt gat cat acc tta tat gat ggg aac act gca ctt tat ata tgt gag              432
Cys Asp His Thr Leu Tyr Asp Gly Asn Thr Ala Leu Tyr Ile Cys Glu
    130                 135                 140 gat ttg atc aca ata ttg aat gat cgt gat atc cca gtt gat aga att              480
Asp Leu Ile Thr Ile Leu Asn Asp Arg Asp Ile Pro Val Asp Arg Ile
145                 150                 155                 160 cca gat att aaa cca tat cat gat cta tta aaa cca aaa ctt gga cat              528
Pro Asp Ile Lys Pro Tyr His Asp Leu Leu Lys Pro Lys Leu Gly His
                165                 170                 175 aca atc aaa act gtc atc caa act ttt gca cca aaa tgg gct tat cct              576
Thr Ile Lys Thr Val Ile Gln Thr Phe Ala Pro Lys Trp Ala Tyr Pro
            180                 185                 190 tta gtt aat ctg att tat aga cca aaa agt gaa ttt gaa act ggt gca              624
Leu Val Asn Leu Ile Tyr Arg Pro Lys Ser Glu Phe Glu Thr Gly Ala
        195                 200                 205 tat gat gat tgg gga gta act cat aaa att gaa aga aca aca aat aaa              672
Tyr Asp Asp Trp Gly Val Thr His Lys Ile Glu Arg Thr Thr Asn Lys
    210                 215                 220 tta aag cac tta att aca ata act aat gaa gaa ttt tcc ata att aaa              720
Leu Lys His Leu Ile Thr Ile Thr Asn Glu Glu Phe Ser Ile Ile Lys
225                 230                 235                 240 aaa tta aca aaa tca cat ggt gta aat ttc aca gca ttt tgg gca tat              768
Lys Leu Thr Lys Ser His Gly Val Asn Phe Thr Ala Phe Trp Ala Tyr
                245                 250                 255 atc aat gtt ctt gca gtt gca caa ttg gga aag tca gct gtt gat tta              816
Ile Asn Val Leu Ala Val Ala Gln Leu Gly Lys Ser Ala Val Asp Leu
            260                 265                 270 tca att cca ttc aat atg aga acc aat tta tta cca cca gaa tat tta              864
Ser Ile Pro Phe Asn Met Arg Thr Asn Leu Leu Pro Pro Glu Tyr Leu
        275                 280                 285 aga tgg tat ggt tta tta gtt tca cat gtt act tta aat gta cat acc              912
Arg Trp Tyr Gly Leu Leu Val Ser His Val Thr Leu Asn Val His Thr
    290                 295                 300 aaa gtt gat cat gat tca att gac tgg gat ttt gtt aga ttt tta aat              960
Lys Val Asp His Asp Ser Ile Asp Trp Asp Phe Val Arg Phe Leu Asn
305                 310                 315                 320 ggt agt gtt gca cat aaa tac caa gta aaa caa tca caa atg ctt gga             1008
Gly Ser Val Ala His Lys Tyr Gln Val Lys Gln Ser Gln Met Leu Gly
                325                 330                 335 atg att aaa tat gtt agt gct cgt gga ctt att gaa tca gct tta aaa             1056
Met Ile Lys Tyr Val Ser Ala Arg Gly Leu Ile Glu Ser Ala Leu Lys
            340                 345                 350 tca cca aga aaa ggt gga tta gaa gtt tca aac ttg gga ttg aga gtc             1104
Ser Pro Arg Lys Gly Gly Leu Glu Val Ser Asn Leu Gly Leu Arg Val
        355                 360                 365 gat cca gat ggt gaa tca tgg aaa aaa tat acc cct gaa gaa ttt ttc             1152
Asp Pro Asp Gly Glu Ser Trp Lys Lys Tyr Thr Pro Glu Glu Phe Phe
    370                 375                 380 ttt tct ttg cca aat gat ctt tca ggt tat aat gtt tca aat gct gtg             1200
Phe Ser Leu Pro Asn Asp Leu Ser Gly Tyr Asn Val Ser Asn Ala Val
385                 390                 395                 400 att tca agt aaa act aaa aca aat att att tta gac ggt gtt cca gaa             1248
Ile Ser Ser Lys Thr Lys Thr Asn Ile Ile Leu Asp Gly Val Pro Glu
                405                 410                 415 ttt gca aat gaa ttt cca acg tat gca aat aac gtt gaa aca att ttg             1296
Phe Ala Asn Glu Phe Pro Thr Tyr Ala Asn Asn Val Glu Thr Ile Leu
            420                 425                 430
```

```
                                      -continued aga aat gca atc aat ggg tat tat gaa taa                              1326
Arg Asn Ala Ile Asn Gly Tyr Tyr Glu
        435                 440

<210> SEQ ID NO 2
<211> LENGTH: 441
<212> TYPE: PRT
<213> ORGANISM: Wickerhamomyces ciferrii

<400> SEQUENCE: 2

Met Val Ala Gly Pro Asn Lys Asp Leu Glu Asn Leu Glu Arg Met Met
1               5                   10                  15

Tyr Trp Lys Thr Thr Leu Lys Ala Trp Ser Cys Phe Leu Val Gly Ala
            20                  25                  30

Lys Leu Asn Glu Lys Leu Glu Thr Asp Asp Ile Leu Lys Gly Ile His
        35                  40                  45

Lys Leu Phe Thr Leu Arg Val Gln Leu Arg Leu Asn Val Phe Gln Tyr
    50                  55                  60

Pro Lys Lys Arg Phe Val Thr Glu Glu Ile Asn Gly Trp Ser Asp Asp
65                  70                  75                  80

Phe Val Asp Phe Val Asp Tyr Pro Thr Asp Asp Phe Asp Ile Ile Glu
                85                  90                  95

Ala Phe Lys Gln Gln His Asn Gln Tyr Phe Glu Leu Gly Val Gln Lys
            100                 105                 110

Pro Leu Trp Lys Leu Val Val Leu Asn His Gln Tyr Leu Val Ile Leu
        115                 120                 125

Cys Asp His Thr Leu Tyr Asp Gly Asn Thr Ala Leu Tyr Ile Cys Glu
    130                 135                 140

Asp Leu Ile Thr Ile Leu Asn Asp Arg Asp Ile Pro Val Asp Arg Ile
145                 150                 155                 160

Pro Asp Ile Lys Pro Tyr His Asp Leu Leu Lys Pro Lys Leu Gly His
                165                 170                 175

Thr Ile Lys Thr Val Ile Gln Thr Phe Ala Pro Lys Trp Ala Tyr Pro
            180                 185                 190

Leu Val Asn Leu Ile Tyr Arg Pro Lys Ser Glu Phe Glu Thr Gly Ala
        195                 200                 205

Tyr Asp Asp Trp Gly Val Thr His Lys Ile Glu Arg Thr Thr Asn Lys
    210                 215                 220

Leu Lys His Leu Ile Thr Ile Thr Asn Glu Glu Phe Ser Ile Ile Lys
225                 230                 235                 240

Lys Leu Thr Lys Ser His Gly Val Asn Phe Thr Ala Phe Trp Ala Tyr
                245                 250                 255

Ile Asn Val Leu Ala Val Ala Gln Leu Gly Lys Ser Ala Val Asp Leu
            260                 265                 270

Ser Ile Pro Phe Asn Met Arg Thr Asn Leu Leu Pro Pro Glu Tyr Leu
        275                 280                 285

Arg Trp Tyr Gly Leu Leu Val Ser His Val Thr Leu Asn Val His Thr
    290                 295                 300

Lys Val Asp His Asp Ser Ile Asp Trp Asp Phe Val Arg Phe Leu Asn
305                 310                 315                 320

Gly Ser Val Ala His Lys Tyr Gln Val Lys Gln Ser Gln Met Leu Gly
                325                 330                 335

Met Ile Lys Tyr Val Ser Ala Arg Gly Leu Ile Glu Ser Ala Leu Lys
            340                 345                 350

Ser Pro Arg Lys Gly Gly Leu Glu Val Ser Asn Leu Gly Leu Arg Val
```

```
                355                 360                 365
Asp Pro Asp Gly Glu Ser Trp Lys Lys Tyr Thr Pro Glu Phe Phe
    370                 375                 380

Phe Ser Leu Pro Asn Asp Leu Ser Gly Tyr Asn Val Ser Asn Ala Val
385                 390                 395                 400

Ile Ser Ser Lys Thr Lys Thr Asn Ile Ile Leu Asp Gly Val Pro Glu
                405                 410                 415

Phe Ala Asn Glu Phe Pro Thr Tyr Ala Asn Asn Val Gly Thr Ile Leu
            420                 425                 430

Arg Asn Ala Ile Asn Gly Tyr Tyr Glu
            435                 440

<210> SEQ ID NO 3
<211> LENGTH: 1407
<212> TYPE: DNA
<213> ORGANISM: Saccharomyces cerevisiae
<220> FEATURE:
<221> NAME/KEY: CDS
<222> LOCATION: (1)..(1407)

<400> SEQUENCE: 3 atg aat ctt aaa ctt tct gct att gaa agt tac ttt ttc cat aga agc     48
Met Asn Leu Lys Leu Ser Ala Ile Glu Ser Tyr Phe Phe His Arg Ser
1               5                   10                  15 aga cta aat ttg cat tca tgt ttt tat gtc gga atc aaa ctc aac gaa     96
Arg Leu Asn Leu His Ser Cys Phe Tyr Val Gly Ile Lys Leu Asn Glu
            20                  25                  30 ttg ccc aaa aaa agt caa ctg ata gcg gct ctt aag tat act gta atc    144
Leu Pro Lys Lys Ser Gln Leu Ile Ala Ala Leu Lys Tyr Thr Val Ile
        35                  40                  45 caa cat gaa cgt ttg act tgt aat gta ttc tat gat gaa ttg aaa aag    192
Gln His Glu Arg Leu Thr Cys Asn Val Phe Tyr Asp Glu Leu Lys Lys
    50                  55                  60 gaa aac ttc cta caa aac att ctt gag cca ctg aaa ttt tgc gat cta    240
Glu Asn Phe Leu Gln Asn Ile Leu Glu Pro Leu Lys Phe Cys Asp Leu
65                  70                  75                  80 gta gaa tac cgc cac gat tgg gac cag tta ggg gaa acc gaa att aac    288
Val Glu Tyr Arg His Asp Trp Asp Gln Leu Gly Glu Thr Glu Ile Asn
                85                  90                  95 cac atc ttt caa agg tat aac ttt tca tac aac gag aat aaa cct tta    336
His Ile Phe Gln Arg Tyr Asn Phe Ser Tyr Asn Glu Asn Lys Pro Leu
            100                 105                 110 tgg aaa att ctg atc ctc cct aat caa aat caa atg cta ttg ctg aca    384
Trp Lys Ile Leu Ile Leu Pro Asn Gln Asn Gln Met Leu Leu Leu Thr
        115                 120                 125 gat cat gtt ctc atg gat ggg atg tcc gct att cat gtg tgg gaa acg    432
Asp His Val Leu Met Asp Gly Met Ser Ala Ile His Val Trp Glu Thr
    130                 135                 140 ttt atg gaa ggc cta cag atg caa cag ccg gtt gaa att gat gaa aca    480
Phe Met Glu Gly Leu Gln Met Gln Gln Pro Val Glu Ile Asp Glu Thr
145                 150                 155                 160 ata tat tca cca tca tta aat tca tca act gaa aaa ata atg tca gcc    528
Ile Tyr Ser Pro Ser Leu Asn Ser Ser Thr Glu Lys Ile Met Ser Ala
                165                 170                 175 cca cta tac gga gat tgg ccc ata cct tgg aat tgg cat ata gtg cga    576
Pro Leu Tyr Gly Asp Trp Pro Ile Pro Trp Asn Trp His Ile Val Arg
            180                 185                 190 caa ttg gtc agt aga cta cat tat tgg ttt cca caa aca gtc gta aaa    624
Gln Leu Val Ser Arg Leu His Tyr Trp Phe Pro Gln Thr Val Val Lys
        195                 200                 205
```

```
aac aat aga aat tta atc caa ttt gcc aac tac tca ttt cca aaa gac      672
Asn Asn Arg Asn Leu Ile Gln Phe Ala Asn Tyr Ser Phe Pro Lys Asp
    210                 215                 220 ctg ctg gat gat aaa ccg agc gat gga act caa aaa tac aaa gtt aaa      720
Leu Leu Asp Asp Lys Pro Ser Asp Gly Thr Gln Lys Tyr Lys Val Lys
225                 230                 235                 240 aac acg aac cat caa tgg gag ttt cga tta tcg ccg acc cat ctc aac      768
Asn Thr Asn His Gln Trp Glu Phe Arg Leu Ser Pro Thr His Leu Asn
                245                 250                 255 gac att tta caa gaa tgc aag gcc aat aat act tcg ttg act tcc ctt      816
Asp Ile Leu Gln Glu Cys Lys Ala Asn Asn Thr Ser Leu Thr Ser Leu
            260                 265                 270 tta ggt gcc ctg gtc tgc acc agt ttc gaa aaa ata gct gca cat gag      864
Leu Gly Ala Leu Val Cys Thr Ser Phe Glu Lys Ile Ala Ala His Glu
        275                 280                 285 tat acc gga tca ttt ttg aaa att gaa tta cca atg aat att aga aag      912
Tyr Thr Gly Ser Phe Leu Lys Ile Glu Leu Pro Met Asn Ile Arg Lys
    290                 295                 300 cct ttt gaa cga gtc ttg aaa tta cct tca gat gat aag ctc gcc gtg      960
Pro Phe Glu Arg Val Leu Lys Leu Pro Ser Asp Asp Lys Leu Ala Val
305                 310                 315                 320 gga aat ttt att gcg gtc ata gaa ttc aac cat aaa cta cat caa aac     1008
Gly Asn Phe Ile Ala Val Ile Glu Phe Asn His Lys Leu His Gln Asn
                325                 330                 335 cgt gga ata tgg gat atc gct tct caa att caa agg gcc ata aga agc     1056
Arg Gly Ile Trp Asp Ile Ala Ser Gln Ile Gln Arg Ala Ile Arg Ser
            340                 345                 350 agt tcc gag gat aaa ata ata gat aaa gta aac gaa gta aag tta ttg     1104
Ser Ser Glu Asp Lys Ile Ile Asp Lys Val Asn Glu Val Lys Leu Leu
        355                 360                 365 gag gtt att tct tct caa caa tac ata gaa gat aaa att agc ttg aat     1152
Glu Val Ile Ser Ser Gln Gln Tyr Ile Glu Asp Lys Ile Ser Leu Asn
    370                 375                 380 aac gga cct tct tcc aca ttt gaa gta aca aac tta gga ttt caa aca     1200
Asn Gly Pro Ser Ser Thr Phe Glu Val Thr Asn Leu Gly Phe Gln Thr
385                 390                 395                 400 ttt aaa gat gca tgc aac acc agt tta ccg ttt tat ata gtg gat gct     1248
Phe Lys Asp Ala Cys Asn Thr Ser Leu Pro Phe Tyr Ile Val Asp Ala
                405                 410                 415 aca ttc aac gag ccg caa gga ata tct tca att ttc tca cta agc gta     1296
Thr Phe Asn Glu Pro Gln Gly Ile Ser Ser Ile Phe Ser Leu Ser Val
            420                 425                 430 atc tct act cct ggt aac gga cta cat tgt tgt atc agt tat cca aat     1344
Ile Ser Thr Pro Gly Asn Gly Leu His Cys Cys Ile Ser Tyr Pro Asn
        435                 440                 445 act ctc act aaa gtg cta gaa ccc cac tgg caa tat atg aaa gat tac     1392
Thr Leu Thr Lys Val Leu Glu Pro His Trp Gln Tyr Met Lys Asp Tyr
    450                 455                 460 tta aat tta tac tag                                                 1407
Leu Asn Leu Tyr
465
```

<210> SEQ ID NO 4
<211> LENGTH: 468
<212> TYPE: PRT
<213> ORGANISM: Saccharomyces cerevisiae

<400> SEQUENCE: 4

```
Met Asn Leu Lys Leu Ser Ala Ile Glu Ser Tyr Phe Phe His Arg Ser
1               5                   10                  15
```

-continued

Arg Leu Asn Leu His Ser Cys Phe Tyr Val Gly Ile Lys Leu Asn Glu
            20                  25                  30

Leu Pro Lys Ser Gln Leu Ile Ala Ala Leu Lys Tyr Thr Val Ile
        35                  40                  45

Gln His Glu Arg Leu Thr Cys Asn Val Phe Tyr Asp Glu Leu Lys Lys
 50                  55                  60

Glu Asn Phe Leu Gln Asn Ile Leu Glu Pro Leu Lys Phe Cys Asp Leu
65                   70                  75                  80

Val Glu Tyr Arg His Asp Trp Asp Gln Leu Gly Glu Thr Glu Ile Asn
                85                  90                  95

His Ile Phe Gln Arg Tyr Asn Phe Ser Tyr Asn Glu Asn Lys Pro Leu
            100                 105                 110

Trp Lys Ile Leu Ile Leu Pro Asn Gln Asn Gln Met Leu Leu Leu Thr
                115                 120                 125

Asp His Val Leu Met Asp Gly Met Ser Ala Ile His Val Trp Glu Thr
            130                 135                 140

Phe Met Glu Gly Leu Gln Met Gln Gln Pro Val Gly Ile Asp Glu Thr
145                 150                 155                 160

Ile Tyr Ser Pro Ser Leu Asn Ser Ser Thr Glu Lys Ile Met Ser Ala
                165                 170                 175

Pro Leu Tyr Gly Asp Trp Pro Ile Pro Trp Asn Trp His Ile Val Arg
            180                 185                 190

Gln Leu Val Ser Arg Leu His Tyr Trp Phe Pro Gln Thr Val Val Lys
            195                 200                 205

Asn Asn Arg Asn Leu Ile Gln Phe Ala Asn Tyr Ser Phe Pro Lys Asp
        210                 215                 220

Leu Leu Asp Asp Lys Pro Ser Asp Gly Thr Gln Lys Tyr Lys Val Lys
225                 230                 235                 240

Asn Thr Asn His Gln Trp Glu Phe Arg Leu Ser Pro Thr His Leu Asn
            245                 250                 255

Asp Ile Leu Gln Glu Cys Lys Ala Asn Asn Thr Ser Leu Thr Ser Leu
            260                 265                 270

Leu Gly Ala Leu Val Cys Thr Ser Phe Glu Lys Ile Ala Ala His Glu
            275                 280                 285

Tyr Thr Gly Ser Phe Leu Lys Ile Glu Leu Pro Met Asn Ile Arg Lys
        290                 295                 300

Pro Phe Glu Arg Val Leu Lys Leu Pro Ser Asp Asp Lys Leu Ala Val
305                 310                 315                 320

Gly Asn Phe Ile Ala Val Ile Glu Phe Asn His Lys Leu His Gln Asn
            325                 330                 335

Arg Gly Ile Trp Asp Ile Ala Ser Gln Ile Gln Arg Ala Ile Arg Ser
            340                 345                 350

Ser Ser Glu Asp Lys Ile Ile Asp Lys Val Asn Glu Val Lys Leu Leu
        355                 360                 365

Glu Val Ile Ser Ser Gln Gln Tyr Ile Glu Asp Lys Ile Ser Leu Asn
        370                 375                 380

Asn Gly Pro Ser Ser Thr Phe Glu Val Thr Asn Leu Gly Phe Gln Thr
385                 390                 395                 400

Phe Lys Asp Ala Cys Asn Thr Ser Leu Pro Phe Tyr Ile Val Asp Ala
            405                 410                 415

Thr Phe Asn Glu Pro Gln Gly Ile Ser Ser Ile Phe Ser Leu Ser Val
            420                 425                 430

```
Ile Ser Thr Pro Gly Asn Gly Leu His Cys Cys Ile Ser Tyr Pro Asn
            435                 440                 445

Thr Leu Thr Lys Val Leu Glu Pro His Trp Gln Tyr Met Lys Asp Tyr
    450                 455                 460

Leu Asn Leu Tyr
465

<210> SEQ ID NO 5
<211> LENGTH: 1338
<212> TYPE: DNA
<213> ORGANISM: Pichia pastris
<220> FEATURE:
<221> NAME/KEY: CDS
<222> LOCATION: (1)..(1338)

<400> SEQUENCE: 5 atg gaa ggt act acg agt caa gcg ggc agg agg act ttg agg cca att    48
Met Glu Gly Thr Thr Ser Gln Ala Gly Arg Arg Thr Leu Arg Pro Ile
1               5                   10                  15 gaa gaa tac aac tat cag aga aac gtt ctg aag aca tac tcc tgt ttc    96
Glu Glu Tyr Asn Tyr Gln Arg Asn Val Leu Lys Thr Tyr Ser Cys Phe
            20                  25                  30 att gtg gct tca aaa ttg agt gaa tgc gtt gat aaa gag gtt ctt tta   144
Ile Val Ala Ser Lys Leu Ser Glu Cys Val Asp Lys Glu Val Leu Leu
        35                  40                  45 ttt gga att cag aaa ctg gtg gca agc cgt aaa cag ctg aga ctg aat   192
Phe Gly Ile Gln Lys Leu Val Ala Ser Arg Lys Gln Leu Arg Leu Asn
    50                  55                  60 gtg ttc aaa gaa gac ggc acc aac gac cta tat ttg cag gaa ata tcg   240
Val Phe Lys Glu Asp Gly Thr Asn Asp Leu Tyr Leu Gln Glu Ile Ser
65                  70                  75                  80 gat tgg agc gtt gat gat gtt gtg gag ttc aaa acg ggt agt gat att   288
Asp Trp Ser Val Asp Asp Val Val Glu Phe Lys Thr Gly Ser Asp Ile
                85                  90                  95 gtg gag gag atc ggt atg gct cat aga tac tgc ttt gta act gca atc   336
Val Glu Glu Ile Gly Met Ala His Arg Tyr Cys Phe Val Thr Ala Ile
            100                 105                 110 aac aag ccc ttg tgg aaa cta gtc gtt ctc aat tct caa tgg tta tta   384
Asn Lys Pro Leu Trp Lys Leu Val Val Leu Asn Ser Gln Trp Leu Leu
        115                 120                 125 tta cag tgt gac cat acg cta cta gac ggg aat tct gct gct ttt ttc   432
Leu Gln Cys Asp His Thr Leu Leu Asp Gly Asn Ser Ala Ala Phe Phe
    130                 135                 140 cac gaa gaa ttg gtc tgt cta ttg aat aat caa cca att ggc aaa gac   480
His Glu Glu Leu Val Cys Leu Leu Asn Asn Gln Pro Ile Gly Lys Asp
145                 150                 155                 160 tta gag gag gag tcg caa ctc tca aaa ttc aca aca cct tca act aga   528
Leu Glu Glu Glu Ser Gln Leu Ser Lys Phe Thr Thr Pro Ser Thr Arg
                165                 170                 175 tac ctg atc gga tgt ctg ttc agt gaa ttc agc ccc aag tgg ttg tca   576
Tyr Leu Ile Gly Cys Leu Phe Ser Glu Phe Ser Pro Lys Trp Leu Ser
            180                 185                 190 aat tgg ttt ggg aaa cta ggc aaa atg cca ttc aca gag aaa tct cag   624
Asn Trp Phe Gly Lys Leu Gly Lys Met Pro Phe Thr Glu Lys Ser Gln
        195                 200                 205 tat caa acg gat gat cca agt tgg aat atc agt gtc aag tct ccc ata   672
Tyr Gln Thr Asp Asp Pro Ser Trp Asn Ile Ser Val Lys Ser Pro Ile
    210                 215                 220 aaa gat aac gag ttc aag acg tta aag cat cta atc aca ata aat acc   720
Lys Asp Asn Glu Phe Lys Thr Leu Lys His Leu Ile Thr Ile Asn Thr
225                 230                 235                 240
```

```
caa gaa ttc att aag ttg aag tcc tta ctg aag gcg caa tcg gtc tcc      768
Gln Glu Phe Ile Lys Leu Lys Ser Leu Leu Lys Ala Gln Ser Val Ser
                245                 250                 255 ttc acg agt ttc tgg cta tat ttg aac ctt tca gtg ctt tct cag ttt      816
Phe Thr Ser Phe Trp Leu Tyr Leu Asn Leu Ser Val Leu Ser Gln Phe
            260                 265                 270 act caa ctc tct tta aac tgt agc att cca gtg aat ttg aga acc tta      864
Thr Gln Leu Ser Leu Asn Cys Ser Ile Pro Val Asn Leu Arg Thr Leu
        275                 280                 285 tta gac aaa aga aat gct aag agt tat gga cta ttc gtt tct gct gtg      912
Leu Asp Lys Arg Asn Ala Lys Ser Tyr Gly Leu Phe Val Ser Ala Val
    290                 295                 300 gaa ctc aag tta tcc acg aga cta gtc tct cat gaa tca ttc gat tgg      960
Glu Leu Lys Leu Ser Thr Arg Leu Val Ser His Glu Ser Phe Asp Trp
305                 310                 315                 320 aat tac gtc aga tac ata caa tcc cat tta tct cca gtt aaa ctg gaa     1008
Asn Tyr Val Arg Tyr Ile Gln Ser His Leu Ser Pro Val Lys Leu Glu
                325                 330                 335 gaa agt gct cag tta gtt gga atg ctc aac tat gta aac gcc aag gac     1056
Glu Ser Ala Gln Leu Val Gly Met Leu Asn Tyr Val Asn Ala Lys Asp
            340                 345                 350 tat cta ctc cag aaa tct tcc aaa cca aga act tgt act ctg gag atc     1104
Tyr Leu Leu Gln Lys Ser Ser Lys Pro Arg Thr Cys Thr Leu Glu Ile
        355                 360                 365 tct aat cta gga ctc cga gag gac tac aaa aac act gcc gct caa ccc     1152
Ser Asn Leu Gly Leu Arg Glu Asp Tyr Lys Asn Thr Ala Ala Gln Pro
    370                 375                 380 tac ctt aat gaa atc att ttc tcc caa cca aat aac att act ggt cca     1200
Tyr Leu Asn Glu Ile Ile Phe Ser Gln Pro Asn Asn Ile Thr Gly Pro
385                 390                 395                 400 tat ata aca aac gat atg gcc tcc act tca gaa cag gtg aat att cta     1248
Tyr Ile Thr Asn Asp Met Ala Ser Thr Ser Glu Gln Val Asn Ile Leu
                405                 410                 415 atc ggt gca gtc cca gag tgt gga tat ttt tac gat ctt tat aca tct     1296
Ile Gly Ala Val Pro Glu Cys Gly Tyr Phe Tyr Asp Leu Tyr Thr Ser
            420                 425                 430 ggg ctg gaa gcc tta ctg aat gaa ttc att cgc gac att taa             1338
Gly Leu Glu Ala Leu Leu Asn Glu Phe Ile Arg Asp Ile
        435                 440                 445

<210> SEQ ID NO 6
<211> LENGTH: 445
<212> TYPE: PRT
<213> ORGANISM: Pichia pastris

<400> SEQUENCE: 6

Met Glu Gly Thr Thr Ser Gln Ala Gly Arg Arg Thr Leu Arg Pro Ile
1               5                   10                  15

Glu Glu Tyr Asn Tyr Gln Arg Asn Val Leu Lys Thr Tyr Ser Cys Phe
            20                  25                  30

Ile Val Ala Ser Lys Leu Ser Glu Cys Val Asp Lys Val Leu Leu
        35                  40                  45

Phe Gly Ile Gln Lys Leu Val Ala Ser Arg Lys Gln Leu Arg Leu Asn
    50                  55                  60

Val Phe Lys Glu Asp Gly Thr Asn Asp Leu Tyr Leu Gln Glu Ile Ser
65                  70                  75                  80

Asp Trp Ser Val Asp Val Val Glu Phe Lys Thr Gly Ser Asp Ile
            85                  90                  95
```

```
Val Glu Glu Ile Gly Met Ala His Arg Tyr Cys Phe Val Thr Ala Ile
            100                 105                 110

Asn Lys Pro Leu Trp Lys Leu Val Val Leu Asn Ser Gln Trp Leu Leu
        115                 120                 125

Leu Gln Cys Asp His Thr Leu Leu Asp Gly Asn Ser Ala Ala Phe Phe
    130                 135                 140

His Glu Glu Leu Val Cys Leu Leu Asn Asn Gln Pro Ile Gly Lys Asp
145                 150                 155                 160

Leu Glu Glu Glu Ser Gln Leu Ser Lys Phe Thr Thr Pro Ser Thr Arg
                165                 170                 175

Tyr Leu Ile Gly Cys Leu Phe Ser Glu Phe Ser Pro Lys Trp Leu Ser
            180                 185                 190

Asn Trp Phe Gly Lys Leu Gly Lys Met Pro Phe Thr Glu Lys Ser Gln
        195                 200                 205

Tyr Gln Thr Asp Asp Pro Ser Trp Asn Ile Ser Val Lys Ser Pro Ile
    210                 215                 220

Lys Asp Asn Glu Phe Lys Thr Leu Lys His Leu Ile Thr Ile Asn Thr
225                 230                 235                 240

Gln Glu Phe Ile Lys Leu Lys Ser Leu Leu Lys Ala Gln Ser Val Ser
                245                 250                 255

Phe Thr Ser Phe Trp Leu Tyr Leu Asn Leu Ser Val Leu Ser Gln Phe
            260                 265                 270

Thr Gln Leu Ser Leu Asn Cys Ser Ile Pro Val Asn Leu Arg Thr Leu
        275                 280                 285

Leu Asp Lys Arg Asn Ala Lys Ser Tyr Gly Leu Phe Val Ser Ala Val
    290                 295                 300

Glu Leu Lys Leu Ser Thr Arg Leu Val Ser His Glu Ser Phe Asp Trp
305                 310                 315                 320

Asn Tyr Val Arg Tyr Ile Gln Ser His Leu Ser Pro Val Lys Leu Glu
                325                 330                 335

Glu Ser Ala Gln Leu Val Gly Met Leu Asn Tyr Val Asn Ala Lys Asp
            340                 345                 350

Tyr Leu Leu Gln Lys Ser Ser Lys Pro Arg Thr Cys Thr Leu Glu Ile
        355                 360                 365

Ser Asn Leu Gly Leu Arg Glu Asp Tyr Lys Asn Thr Ala Ala Gln Pro
    370                 375                 380

Tyr Leu Asn Glu Ile Ile Phe Ser Gln Pro Asn Asn Ile Thr Gly Pro
385                 390                 395                 400

Tyr Ile Thr Asn Asp Met Ala Ser Thr Ser Glu Gln Val Asn Ile Leu
                405                 410                 415

Ile Gly Ala Val Pro Glu Cys Gly Tyr Phe Tyr Asp Leu Tyr Thr Ser
            420                 425                 430

Gly Leu Glu Ala Leu Leu Asn Glu Phe Ile Arg Asp Ile
        435                 440                 445

<210> SEQ ID NO 7
<211> LENGTH: 1326
<212> TYPE: DNA
<213> ORGANISM: Artificial sequence
<220> FEATURE:
<223> OTHER INFORMATION: synthetic polynucleotide

<400> SEQUENCE: 7
atggtggctg ggccgaacaa ggatttggag aatctggaga ggatgatgta ttggaagaca     60
accctgaagg cgtggagttg cttttttggtg ggggcaaagc ttaacgagaa attggaaact    120
```

```
gatgacattc ttaaggggat tcataaattg ttcacactga gagttcagtt gcgcctgaac      180
gtctttcaat accccaagaa aagattcgtt accgaggaaa ttaatgggtg gtcagatgac      240
tttgtggatt tcgttgacta cccgacggat gactttgata ttatcgaggc attcaagcag      300
caacacaacc agtatttcga attggggtg caaaagcctc tctggaaact tgttgtcttg       360
aatcatcagt acctggttat cctctgcgat cacaccctgt acgacgggaa cacggcgctc      420
tatatttgtg aggatctgat taccatcctc aatgatcgag acatcccgt cgatcgtatt      480 cccgacatca agccgtatca tgacctcctt aagccgaaac ttgggcacac cattaagacg      540
gttatccaaa catttgctcc taaatgggcc tacccacttg tcaatttgat ctaccgtcca      600
aagtctgagt tcgaaaccgg ggcctacgat gactggggg ttacgcataa aatcgagagg      660
actacaaaca agctgaaaca cctcattacc atcacgaacg aggaattttc aattatcaag      720
aaacttacta agtcgcatgg ggtcaacttt acagcattct gggcgtatat taatgtcctg     780
gctgtggccc agctcgggaa atccgctgtg gacttgagta tcccttcaa catgaggact      840 aatttgctgc ctccagaata ccttagatgg tatgggctcc ttgttagcca tgtcactttg      900
aacgtgcata caaaggttga tcacgactct attgattggg actttgttcg attcctgaat     960
gggtccgtgg cccacaagta ccaagttaaa cagagtcaaa tgctcgggat gattaaatat    1020
gtctctgcac gcgggcttat cgagtcagcg ttgaagtcgc ctcgaaaagg ggggctggaa    1080
gtcagcaacc tcgggcttag agttgatcct gacggggagt catggaagaa atacacacct    1140
gaggaattct tttctcgct tccaaatgat ttgtctgggt ataacgtcag caatgctgtg     1200
atctctagca agactaaaac aaacattatc ctcgacgggg ttcccgagtt tgccaatgaa    1260
ttcccgacct atgcgaacaa tgtggaaact atcctccgta acgctatcaa tgggtattat    1320
gaatga                                                              1326

<210> SEQ ID NO 8
<211> LENGTH: 1407
<212> TYPE: DNA
<213> ORGANISM: Artificial sequence
<220> FEATURE:
<223> OTHER INFORMATION: synthetic polynucleotide

<400> SEQUENCE: 8
atgaatctca agctgtccgc aatcgaatcg tatttcttcc atcgtagcag gctcaatctc       60
cactcgtgtt tctatgttgg tatcaagctg aacgagcttc aaagaaaag ccagctgatt       120 gctgccctca aatatactgt gatccaacat gaacgactca catgcaatgt ttctacgat       180 gagcttaaga aagaaaactt tttgcaaaac attcttgagc ccttgaagtt ctgtgacctt      240
gttgaatatc gccatgattg ggaccagttg ggcgagactg aaattaacca catcttccaa      300
cgatacaact tctcctacaa cgagaacaag cctctttgga agattcttat cttgccaaac      360
cagaatcaaa tgctcctttt gactgatcat gtcctcatgg acggaatgtc agctattcac      420
gtgtgggaga cattcatgga aggtcttcag atgcagcaac ccgtcgagat tgatgaaact      480
atctatagtc cgtctcttaa ctctagcaca gagaaaatca tgagtgcccc cttgtacgga      540
gactggccta ttccttggaa ttggcatatc gtccgacagc ttgtgtctcg tttgcactac      600
tggttcccgc aaaccgttgt caagaacaat cgtaacttga tccagttcgc taattatagt      660
tttcccaaag atctgctcga tgacaagccg tctgacggca ctcagaagta caaagttaag      720
aacacgaatc atcaatggga gtttaggctg tctcctacac acctgaacga tattctccaa      780
```

| | |
|---|---|
| gaatgcaaag ctaacaatac ctcgctgacg tcccttttgg gcgccctcgt ctgtacctcg | 840 |
| ttcgagaaga tcgcagcgca cgaatatacg ggctcttttcc tcaaaattga gttgcccatg | 900 |
| aacatcagga agccgttcga aagagtgctg aaactccctt cggatgacaa gttggctgtt | 960 |
| ggtaatttca ttgccgtcat cgagtttaac cataaactgc accagaatag aggcatttgg | 1020 |
| gatattgcat ctcagattca aagagcgatc cgctcatcgt ccgaagataa aattatcgac | 1080 |
| aaagtgaatg aggttaaact gctcgaagtg attagttctc agcaatacat tgaggacaag | 1140 |
| atcagcctga acaatggtcc tagctcaact ttcgaagtta caaacctcgg cttccaaacc | 1200 |
| tttaaggatg catgcaatac gtcacttcct ttctatatcg ttgacgcgac ctttaacgag | 1260 |
| ccacagggaa tttcgtccat ctttagcctg tcagtcatta gcacgccagg caacggactc | 1320 |
| cattgctgta tctcataccc taatactctg acaaaagttc ttgagccaca ctggcagtac | 1380 |
| atgaaggact atcttaattt gtactga | 1407 |

<210> SEQ ID NO 9
<211> LENGTH: 1338
<212> TYPE: DNA
<213> ORGANISM: Artificial sequence
<220> FEATURE:
<223> OTHER INFORMATION: synthetic polynucleotide

<400> SEQUENCE: 9

| | |
|---|---|
| atggaaggca ctacaagcca agcaggcaga agaacactcc gtcctatcga agaatacaac | 60 |
| tatcagcgta atgtcctcaa aacctatagc tgcttcattg ttgcttctaa gcttagcgaa | 120 |
| tgtgttgata aagaggtcct ccttttggc atccagaagt tggttgcctc aagaaaacaa | 180 |
| cttcgcttga acgtcttcaa ggaagatgga actaatgacc tgtacctcca ggagatttca | 240 |
| gattggtcgg tcgatgacgt tgtcgagttt aaaactggaa gcgacattgt ggaggaaatc | 300 |
| ggtatggctc atcgttattg cttcgttaca gccatcaaca agcctttgtg gaaactggtg | 360 |
| gttctcaatt ctcagtggtt gctgctccaa tgcgatcata ccctttttgga cggtaacagc | 420 |
| gctgccttct ttcacgagga actggtctgt ctgctcaaca atcagcccat ggcaaggat | 480 |
| ctggaggaag agtcccaact cagtaaattt actacaccgt caacgcgcta cctgatcggc | 540 |
| tgtctcttct ctgaatttag ccctaagtgg ctttcgaatt ggttcggcaa gttgggaaaa | 600 |
| atgccattta ctgagaaatc acagtatcaa acagatgacc cctcgtggaa catttcagtg | 660 |
| aagtcgccga tcaaagacaa tgagttcaag actcttaaac acttgattac tatcaacaca | 720 |
| caggagttta ttaagttgaa atccctttg aaggcacaat cagtctcgtt cacaagttt | 780 |
| tggctttact tgaatctgtc cgtgctgagt cagttcaccc aactctccct taactgcagt | 840 |
| atccccgtta atctccgaac gctgctcgat aagcgtaacg caaaatctta tggcctgttt | 900 |
| gtcagcgcgg tggaattgaa actgtctacc cgcctcgtgt ctcatgagag cttcgactgg | 960 |
| aattacgttc gatatattca gtcacacctg tcgccggtca agctcgaaga gtcggctcaa | 1020 |
| cttgtgggaa tgttgaacta cgttaatgcc aaagattatc ttttgcagaa gtctagcaaa | 1080 |
| cctaggacct gcacgcttga aatctccaac ctcggactta gagaggacta caagaacaca | 1140 |
| gcagcgcagc catatttgaa tgagatcatc ttctctcaac ctaacaacat caccggtcca | 1200 |
| tacatcacga acgacatggc atccaccagt gaacaagtca atattcttat cggtgcggtg | 1260 |
| ccagagtgtg gctacttcta tgatctttat acgtctggct tggaagccct gctcaatgag | 1320 |
| tttattagag acatctag | 1338 |

```
<210> SEQ ID NO 10
<211> LENGTH: 34
<212> TYPE: DNA
<213> ORGANISM: Artificial sequence
<220> FEATURE:
<223> OTHER INFORMATION: synthetic oligonucleotide

<400> SEQUENCE: 10
caactctaca caaatggtgg ctgggccgaa caag                        34

<210> SEQ ID NO 11
<211> LENGTH: 34
<212> TYPE: DNA
<213> ORGANISM: Artificial sequence
<220> FEATURE:
<223> OTHER INFORMATION: synthetic oligonucleotide

<400> SEQUENCE: 11
ctacgaatat tcaatggtgg ctgggccgaa caag                        34

<210> SEQ ID NO 12
<211> LENGTH: 33
<212> TYPE: DNA
<213> ORGANISM: Artificial sequence
<220> FEATURE:
<223> OTHER INFORMATION: synthetic oligonucleotide

<400> SEQUENCE: 12
gagtgagctg tcattcataa tacccattga tag                         33

<210> SEQ ID NO 13
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 13
catccgatgt gtagttaatc attg                                   24

<210> SEQ ID NO 14
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 14
ttgtgtagag ttgttttttgt tg                                    22

<210> SEQ ID NO 15
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 15
ccaaacctga tctttagtga actg                                   24

<210> SEQ ID NO 16
<211> LENGTH: 21
<212> TYPE: DNA
<213> ORGANISM: Artificial sequence
<220> FEATURE:
<223> OTHER INFORMATION: synthetic oligonucleotide
```

```
<400> SEQUENCE: 16
tgaatattcg tagggagaag c                                         21

<210> SEQ ID NO 17
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 17
agctcactcg ttgagagaga gcac                                      24

<210> SEQ ID NO 18
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 18
cgacaggtca tgttatcaag ccgag                                     25

<210> SEQ ID NO 19
<211> LENGTH: 1026
<212> TYPE: DNA
<213> ORGANISM: Escherichia coli

<400> SEQUENCE: 19
atgaaaaagc ctgaactcac cgcgacgtct gtcgagaagt ttctgatcga aaagttcgac   60
agcgtctccg acctgatgca gctctcggag ggcgaagaat ctcgtgcttt cagcttcgat  120
gtaggagggc gtggatacgt cctgcgggta aatagctgcg ccgatggttt ctacaaagat  180
cgttatgttt atcggcactt tgcatcggcc gcgctcccga ttccggaagt gcttgacatt  240
ggggaattca gcgagagcct gacctattgc atctcccgcc gtgcacaggg tgtcacgttg  300
caagacctgc ctgaaaccga actgcccgct gttctgcagc cggtcgcgga ggccatggat  360
gcgatcgctg cggccgatct tagccagacg agcgggttcg cccattcgg accgcaagga  420 atcggtcaat acactacatg gcgtgatttc atatgcgcga ttgctgatcc ccatgtgtat  480
cactggcaaa ctgtgatgga cgacaccgtc agtgcgtccg tcgcgcaggc tctcgatgag  540
ctgatgcttt gggccgagga ctgccccgaa gtccggcacc tcgtgcacgc ggatttcggc  600
tccaacaatg tcctgacgga caatggccgc ataacagcgg tcattactg gagcgaggcg  660 atgttcgggg attcccaata cgaggtcgcc aacatcttct tctggaggcc gtggttggct  720
tgtatggagc agcagacgcg ctacttcgag cggaggcatc cggagcttgc aggatcgccg  780
cggctccggg cgtatatgct ccgcattggt cttgaccaac tctatcagag cttggttgac  840
ggcaatttcg atgatgcagc ttgggcgcag ggtcgatgcg acgcaatcgt ccgatccgga  900
gccgggactg tcgggcgtac acaaatcgcc cgcagaagcg cggccgtctg gaccgatggc  960
tgtgtagaag tacttgccga tagtggaaac cgacgcccca gcactcgtcc gagggcaaag 1020
gaatag                                                           1026

<210> SEQ ID NO 20
<211> LENGTH: 40
<212> TYPE: DNA
<213> ORGANISM: Artificial sequence
<220> FEATURE:
<223> OTHER INFORMATION: synthetic oligonucleotide
```

<400> SEQUENCE: 20
cactactgta gagaaataat atgaaaaagc ctgaactcac                                40

<210> SEQ ID NO 21
<211> LENGTH: 47
<212> TYPE: DNA
<213> ORGANISM: Artificial sequence
<220> FEATURE:
<223> OTHER INFORMATION: synthetic oligonucleotide

<400> SEQUENCE: 21
cattgaagga actgtttgag aaaactattc ctttgccctc ggacgag                       47

<210> SEQ ID NO 22
<211> LENGTH: 38
<212> TYPE: DNA
<213> ORGANISM: Artificial sequence
<220> FEATURE:
<223> OTHER INFORMATION: synthetic oligonucleotide

<400> SEQUENCE: 22
ttaagatctc agcttttcg aaacagctcg caacgatc                                  38

<210> SEQ ID NO 23
<211> LENGTH: 40
<212> TYPE: DNA
<213> ORGANISM: Artificial sequence
<220> FEATURE:
<223> OTHER INFORMATION: synthetic oligonucleotide

<400> SEQUENCE: 23
gtgagttcag gcttttcat attatttctc tacagtagtg                                40

<210> SEQ ID NO 24
<211> LENGTH: 47
<212> TYPE: DNA
<213> ORGANISM: Artificial sequence
<220> FEATURE:
<223> OTHER INFORMATION: synthetic oligonucleotide

<400> SEQUENCE: 24
ctcgtccgag ggcaaaggaa tagttttctc aaacagttcc ttcaatg                       47

<210> SEQ ID NO 25
<211> LENGTH: 37
<212> TYPE: DNA
<213> ORGANISM: Artificial sequence
<220> FEATURE:
<223> OTHER INFORMATION: synthetic oligonucleotide

<400> SEQUENCE: 25
cgatatcttc gtcttcatca tcgtcactat acacatc                                  37

<210> SEQ ID NO 26
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 26
tcgactctag aattcataac ttc                                                 23

<210> SEQ ID NO 27

<210> SEQ ID NO 27
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 27
acgaagatat cgtaccgatc                                               20

<210> SEQ ID NO 28
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 28
acaaatccag ccagcgggtt tg                                            22

<210> SEQ ID NO 29
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 29
atatgtactt ttcaatatga taaac                                         25

<210> SEQ ID NO 30
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 30
gtttcttagc ctcccatgga ag                                            22

<210> SEQ ID NO 31
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 31
cggagaaaat tgttcgatgg atag                                          24

<210> SEQ ID NO 32
<211> LENGTH: 41
<212> TYPE: DNA
<213> ORGANISM: Artificial sequence
<220> FEATURE:
<223> OTHER INFORMATION: synthetic oligonucleotide

<400> SEQUENCE: 32
tattgaaaag tacatatttt tcgaaacagc tcgcaacgat c                       41

<210> SEQ ID NO 33
<211> LENGTH: 39
<212> TYPE: DNA
<213> ORGANISM: Artificial sequence
<220> FEATURE:
<223> OTHER INFORMATION: synthetic oligonucleotide

<400> SEQUENCE: 33
gggaggctaa gaaacttcat catcgtcact atacacatc					39

<210> SEQ ID NO 34
<211> LENGTH: 36
<212> TYPE: DNA
<213> ORGANISM: Artificial sequence
<220> FEATURE:
<223> OTHER INFORMATION: synthetic oligonucleotide

<400> SEQUENCE: 34
ctgatagcga gctcacaaat ccagccagcg ggtttg					36

<210> SEQ ID NO 35
<211> LENGTH: 40
<212> TYPE: DNA
<213> ORGANISM: Artificial sequence
<220> FEATURE:
<223> OTHER INFORMATION: synthetic oligonucleotide

<400> SEQUENCE: 35
actacacatc ggatgatatg tacttttcaa tatgataaac					40

<210> SEQ ID NO 36
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 36
gagctcgcta tcagcctcga ct					22

<210> SEQ ID NO 37
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 37
catccgatgt gtagttaatc attg					24

<210> SEQ ID NO 38
<211> LENGTH: 36
<212> TYPE: DNA
<213> ORGANISM: Artificial sequence
<220> FEATURE:
<223> OTHER INFORMATION: synthetic oligonucleotide

<400> SEQUENCE: 38
gtgacgatga tgaagtttct tagcctccca tggaag					36

<210> SEQ ID NO 39
<211> LENGTH: 37
<212> TYPE: DNA
<213> ORGANISM: Artificial sequence
<220> FEATURE:
<223> OTHER INFORMATION: synthetic oligonucleotide

<400> SEQUENCE: 39
cgatatcttc gtccggagaa aattgttcga tggatag					37

<210> SEQ ID NO 40
<211> LENGTH: 24
<212> TYPE: DNA

```
<213> ORGANISM: Artificial sequence
<220> FEATURE:
<223> OTHER INFORMATION: synthetic oligonucleotide

<400> SEQUENCE: 40
ttcatcatcg tcactataca catc                                          24

<210> SEQ ID NO 41
<211> LENGTH: 21
<212> TYPE: DNA
<213> ORGANISM: Artificial sequence
<220> FEATURE:
<223> OTHER INFORMATION: synthetic oligonucleotide

<400> SEQUENCE: 41
gacgaagata tacgtaccga t                                             21

<210> SEQ ID NO 42
<211> LENGTH: 40
<212> TYPE: DNA
<213> ORGANISM: Artificial sequence
<220> FEATURE:
<223> OTHER INFORMATION: synthetic oligonucleotide

<400> SEQUENCE: 42
acaaaaacaa ctctacacaa atgaatctca agctgtccgc                         40

<210> SEQ ID NO 43
<211> LENGTH: 42
<212> TYPE: DNA
<213> ORGANISM: Artificial sequence
<220> FEATURE:
<223> OTHER INFORMATION: synthetic oligonucleotide

<400> SEQUENCE: 43
tctctctcaa cgagtgagct tcagtacaaa ttaagatagt cc                      42

<210> SEQ ID NO 44
<211> LENGTH: 42
<212> TYPE: DNA
<213> ORGANISM: Artificial sequence
<220> FEATURE:
<223> OTHER INFORMATION: synthetic oligonucleotide

<400> SEQUENCE: 44
acaaaaacaa ctctacacaa atggaaggca ctacaagcca ag                      42

<210> SEQ ID NO 45
<211> LENGTH: 41
<212> TYPE: DNA
<213> ORGANISM: Artificial sequence
<220> FEATURE:
<223> OTHER INFORMATION: synthetic oligonucleotide

<400> SEQUENCE: 45
tctctctcaa cgagtgagct tcagatgtct ctaataaact c                       41

<210> SEQ ID NO 46
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 46
ttgtgtagag ttgttttttgt tg                                           22
```

```
<210> SEQ ID NO 47
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 47
agctcactcg ttgagagaga gcac                                          24
```

METHOD FOR PRODUCING ACETYLATED SPHINGOID BASE

REFERENCE TO SEQUENCE LISTING SUBMITTED ELECTRONICALLY

The content of the electronically submitted sequence listing, file name 2537_1220001_SequenceListing_ascii.txt, size 46,905 bytes; and date of creation Jun. 24, 2016, filed herewith, is incorporated herein by reference in its entirety.

FIELD OF THE INVENTION

The present invention relates to a modified microorganism of the genus *Starmerella* producing an acetylated sphingoid base and a method for producing an acetylated sphingoid base by using the microorganism.

BACKGROUND OF THE INVENTION

Sphingolipid is obtained by biosynthesis starting from a condensation reaction between L-serine and an acyl CoA such as palmitoyl-CoA. The basic structure of a sphingolipid, i.e., a sphingoid base, is mainly synthesized as a molecule having a chain length of 18 carbon atoms and known as e.g., sphingosine, phytosphingosine, dihydrosphingosine (sphinganine) and 6-hydroxy sphingosine. Each of these sphingoid bases is bound to a fatty acid via an amide bond to synthesize a ceramide.

Sphingolipid has many physiological functions. Particularly ceramide and a sphingoid base, which are involved in skin-moisturizing function and skin barrier function, suppress moisture evaporation from the skin and play a role in protecting human bodies from various external stimuli. Phytosphingosine is reported to have a growth inhibitory effect against *Staphyrococcus aureus, Streptococcus pyogenes, Micrococcus luteus, Propionibacterium acnes, Candida albicans* and *Trichophyton mentagrophytes* (Non Patent Literatures 1 and 2). In particular, the antibacterial effect of phytosphingosine on *Propionibacterium acnes* is known to be higher than that of erythromycin, which is one of macrolide antibiotics (Non Patent Literature 3).

It is known that supply of a ceramide or a sphingoid base by external application shows an effect of improving skin properties. Furthermore, it has been confirmed that when phytosphingosine and tetraacetylphytosphingosine, which is an acetylated phytosphingosine, are applied to the skin, they are permeated into the skin and converted into a ceramide (Patent Literature 1). Accordingly, external application of ceramide, a sphingoid base or acetylated phytosphingosine is expected to have an improving effect on skin property and a growth inhibitory effect against microorganisms responsible for infection.

Recently, a technique for specifically analyzing the ceramide composition of skin has been established and it has been found that there are 12 classes (340 or more species) of ceramide molecular species formed by combinations of a fatty acid and a sphingoid base (Non Patent Literature 4). For example, as ceramide NP formed by a combination of a saturated fatty acid and a phytosphingosine, a combination of a fatty acid having a chain length of from 23 to 30 carbon atoms and a phytosphingosine having a chain length of from 16 to 26 carbon atoms is found and a molecule having a chain length of from 40 to 52 carbon atoms in total of the fatty acid and phytosphingosine is known to be present. As ceramide NS formed by a combination of a saturated fatty acid and a sphingosine, a combination of a fatty acid having a chain length of from 16 to 30 carbon atoms and a sphingosine having a chain length of from 16 to 26 carbon atoms is found and a molecule having a chain length of from 40 to 54 carbon atoms in total of the fatty acid and a sphingosine is known to be present (Non Patent Literature 4). It is known that healthy skin contains a large amount of long-chain ceramide; whereas the content of ceramide is lowered in rough skin and additionally the amount of short-chain ceramide is increased (Non Patent Literature 5). From this, usefulness of a long-chain ceramide or a sphingoid base is expected.

However, currently commercially available ceramide, a sphingoid base and acetylated phytosphingosine are extremely expensive, e.g., several tens to several hundreds of thousands of yen per kg. In addition, the length of a carbon chain of them is limited. For example, for ceramide NP and ceramide NS, molecules having 34, 36 or 40 carbon atoms are only available; and for phytosphingosine and sphingosine, molecules having 18 carbon atoms are only available.

Since it is difficult to separate and purify animal- or plant-derived sphingolipids, a method for producing a sphingolipid by yeast fermentation has been recently developed as a method for producing a ceramide and a sphingoid base. Candidate yeast strains include *Pichia ciferrii*; at present *Wickerhamomyces ciferrii, Candida utilis* and *Saccharomyces cerevisiae*, and a method for obtaining tetraacetylphytosphingosine using *Wickerhamomyces ciferrii*, which secrets tetraacetylphytosphingosine out of the yeast cells, has been positively developed (Patent Literature 6). The length of carbon chain of acetylated phytosphingosine produced by this method is mostly 18 carbon atoms. Acetylated phytosphingosine is deacetylated and used as phytosphingosine, or bound to a fatty acid via an amide bond through a chemical synthesis and used as a ceramide.

It has been elucidated by in-vitro analysis of biosynthesis pathway that the rate-limiting steps of tetraacetylphytosphingosine synthesis in *Wickerhamomyces ciferrii* are a condensation reaction between serine and palmitoyl-CoA and an acetylation reaction of phytosphingosine. In addition, two acetylation enzymes for phytosphingosine, SLI1 and ATF2, are found (Non Patent Literature 7). Among them, SLI1 produces triacetylphytosphingosine when it is expressed in *Saccharomyces cerevisiae* (Non Patent Literature 6). From this, it is considered that SLI1 is involved in acetylation of any three sites of 3 hydroxy groups and a single amino group of phytosphingosine.

In the meantime, a microorganism of the genus *Starmerella*, for example, *Starmerella bombicola* (old scientific name: *Candida bombicola*), can produce a significant amount of sugar lipid serving as a biosurfactant out of the cells and is known as a microorganism having high lipid availability (Non Patent Literature 8). However, little is known about whether the microorganism produces a ceramide or a sphingolipid.

[Patent Literature 1] U.S. Pat. No. 5,578,641
[Patent Literature 2] JP-A-9-504434
[Non Patent Literature 1] Bibel D. J. et. al., J. Invest. Dermatol., 98, 269, (1992)
[Non Patent Literature 2] Bibel D. J. et. al., Clin. Exper. Dermatol., 20, 395, (1995)
[Non Patent Literature 3] Park C. et. al., Fragrance journal, 10, 84, (1999)
[Non Patent Literature 4] Masukawa Y. et. al., J. Lipid Res., 49, 1466, (2008)
[Non Patent Literature 5] Ishikawa J. et. al., J. Invest. Dermatol., 130, 2511, (2010)

[Non Patent Literature 6] Veld, F. et. al., Appi. Microbiol, Biotechnol., 97, 8537, (2013)
[Non Patent Literature 7] Barenholz, Y. et. al., Biochim. Biophys. Acta, 306, 341, (1973)
[Non Patent Literature 8] Udo R. et. Al., Biotechnology Letters, 18 (2), 149, (1996)

SUMMARY OF THE INVENTION

The present invention relates to (1) or (2).

(1) A method for producing an acetylated sphingoid base comprising: culturing a microorganism of the genus *Starmerella* to which a xenogeneic gene encoding a polypeptide having an activity to acetylate a sphingoid base is introduced.

(2) A *Starmerella* microorganism to which a xenogeneic gene encoding a polypeptide having an activity to acetylate a sphingoid base is introduced.

BRIEF DESCRIPTION OF DRAWINGS

FIG. 1 is a graph showing the amount of acetylated phytosphingosines expressed where (A) shows production of triacetylphytosphingosine (TriAPS) and (B) shows production of tetraacetylphytosphingosine (TAPS).

DETAILED DESCRIPTION OF THE INVENTION

The present invention relates to providing a means for producing an acetylated sphingoid base by using a modified *Starmerella* microorganism, particularly a modified *Starmerella bombicola*.

The present inventors conducted studies on a *Starmerella* microorganism known as a microorganism having high lipid availability. As a result, they found that the microorganism cannot produce a ceramide or a sphingolipid in an amount sufficient to be available. They further investigated. As a result, they unexpectedly found that an acetylated sphingoid base can be produced in an amount sufficient to be available by introducing a xenogeneic gene encoding a polypeptide having an activity to acetylate a sphingoid base into a microorganism of the genus *Starmerella* and culturing the modified microorganism, and that the length of carbon chain of the product is mostly 19 or 20 carbon atoms, which differs from 18 carbon atoms in case of using *Wickerhamomyces ciferrii*.

According to the present invention, it is possible to produce an acetylated sphingoid base, preferably an acetylated phytosphingosine having a chain length of 19 or 20 carbon atoms, useful as an intermediate for synthesizing a ceramide or a ceramide precursor substance in an amount sufficient to be available by using a *Starmerella* microorganism, which does not basically produce a ceramide or a sphingolipid in an amount sufficient to be available.

In the specification, homology between amino acid sequences refers to the rate (%) of the number of sites at which the identical amino acid residues exists between two amino acid sequences when aligned, relative to the total number of amino acid residues. More specifically, the homology is calculated in accordance with the Lipman-Pearson method (Science, 227, 1435, (1985)) and computationally obtained based on the homology analysis (Search homology) program of genetic information treatment software, Genetyx-Win (Ver. 5.1.1; Software Development) by setting the Unit size to compare (ktup) at 2.

Furthermore, the term "gene" includes not only double-stranded DNA but also single stranded DNA molecules, such as a sense chain and an anti-sense chain, constituting the double-stranded DNA, and is not limited by its length. Furthermore, as the polynucleotide, RNA and DNA can be mentioned as an example. DNA includes cDNA, genomic DNA and synthesis DNA.

In the specification, a gene encoding a polypeptide having an activity to acetylate a sphingoid base is referred to also as an acetyltransferase gene and a gene encoding SLI1 is referred to also as SLI1 gene.

In the specification, "xenogeneic" refers to being derived from a microorganism or an organism classified into the genera except the genus *Starmerella*.

In the present invention, the "sphingoid base" refers to a long-chain amino alcohol having a chain length of from 18 to 20 carbon atoms and having the following group:

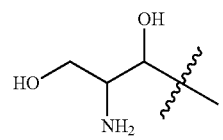

Examples of a sphingoid base having a chain length of 18 carbon atoms include (2S,3S,4R)-2-aminooctadecane-1,3,4-triol (phytosphingosine), (2S,3R,4E)-2-amino-4-octadecene-1,3-diol (sphingosine) and (2S,3R)-2-aminooctadecane-1,3-diol (sphinganine); examples of a sphingoid base having a chain length of 19 carbon atoms include (2S,3S, 4R)-2-aminononadecane-1,3,4-triol (C19 phytosphingosine), (2S,3R,4E)-2-amino-4-nonadecene-1,3-diol (C19 sphingosine) and (2S,3R)-2-aminononadecane-1,3-diol (C19 sphinganine); and examples of a sphingoid base having a chain length of 20 carbon atoms include (2S,3S,4R)-2-aminoicosane-1,3,4-triol (C20 phytosphingosine), (2S,3R, 4E)-2-amino-4-icosene-1,3-diol (C20 sphingosine) and (2S, 3R)-2-aminoicosane-1,3-diol (C20 sphinganine). Among them, phytosphingosine having a chain length of from 19 to 20 carbon atoms is preferable and phytosphingosine having a chain length of 20 carbon atoms is more preferable.

In the present invention, the gene to be introduced into a microorganism of the genus *Starmerella* is not limited as long as the gene encodes a polypeptide having an activity to acetylate a sphingoid base, and is present in a microorganism or an organism classified in the genera except the genus *Starmerella*. Preferable examples include genes found in *Wickerhamomyces ciferrii*, *Saccharomyces cerevisiae* or *Pichia pastoris*, encoding acetyltransferase designated as SLI1, or a polypeptide deduced from the polypeptide, more specifically, a polypeptide consisting of the amino acid sequence selected from the following (a) to (i) and having an acetyltransferase activity:

(a) a polypeptide consisting of the amino acid sequence represented by SEQ ID NO:2, (b) a polypeptide consisting of an amino acid sequence which has a deletion, substitution or addition of one to several amino acid residues in the amino acid sequence represented by SEQ ID NO:2, (c) a polypeptide consisting of the amino acid sequence having a homology of 80% or more with the amino acid sequence represented by SEQ ID NO:2;

(d) a polypeptide consisting of the amino acid sequence represented by SEQ ID NO:4, (e) a polypeptide of an amino acid sequence which has a deletion, substitution or addition of one to several amino acid residues in the amino acid sequence represented by SEQ ID NO:4, (f) a polypeptide consisting of the amino acid sequence having a homology of 80% or more with the amino acid sequence represented by SEQ ID NO:4;

(g) a polypeptide consisting of the amino acid sequence represented by SEQ ID NO:6, (h) a polypeptide consisting of an amino acid sequence which has a deletion, substitution or addition of one to several amino acid residues in the amino acid sequence represented by SEQ ID NO:6, and (i) a polypeptide consisting of the amino acid sequence having a homology of 80% or more with the amino acid sequence represented by SEQ ID NO:6.

Herein, the polypeptide consisting of the amino acid sequence represented by SEQ ID NO:2 is SLI1 derived from *Wickerhamomyces ciferrii*; the polypeptide consisting of the amino acid sequence represented by SEQ ID NO:4 is SLI1 derived from *Saccharomyces cerevisiae*; the polypeptide consisting of the amino acid sequence represented by SEQ ID NO:6 is SLI1 derived from *Pichia pastoris*, and all of them have an acetyltransferase activity, favorably an activity to acetylate a sphingoid base.

Furthermore, "one to several" in the polypeptides of (b), (e) and (h), means from 1 to 80, preferably from 1 to 40, more preferably from 1 to 20, even more preferably from 1 to 10.

The amino acid sequence (c) having a homology of 80% or more with the amino acid sequence represented by SEQ ID NO:2, refers to an amino acid sequence having homology of 80% or more, preferably 90% or more, more preferably 95% or more, with the amino acid sequence of SEQ ID NO:2, when the corresponding sequence thereof is properly aligned with the amino acid sequence represented by SEQ ID NO:2. The amino acid sequence (f) having a homology of 80% or more with the amino acid sequence represented by SEQ ID NO:4 refers to an amino acid sequence having a homology of 80% or more, preferably 90% or more, more preferably 95% or more, with the amino acid sequence of SEQ ID NO:4, when the corresponding sequence thereof is properly aligned with the amino acid sequence represented by SEQ ID NO:4. The amino acid sequence (i) having a homology of 80% or more with the amino acid sequence represented by SEQ ID NO:6 refers to an amino acid sequence having a homology of 80% or more, preferably 90% or more, more preferably 95% or more, with the amino acid sequence of SEQ ID NO:6, when the corresponding sequence thereof is properly aligned with the amino acid sequence represented by SEQ ID NO:6.

The genes encoding polypeptides (a) to (i) may have any selected codons as long as the amino acid sequence of the peptide corresponds to the amino acid sequences (a) to (i). For example, codons suitable for a microorganism of the genus *Starmerella* are preferably selected.

The acetyltransferase activity, specifically, includes an activity to catalyze an acetylation reaction with a sphingoid base, preferably an activity to catalyze an acetylation reaction with a hydroxy group and an amino group of phytosphingosine.

The gene of the present invention can be easily obtained by a customary PCR method using primers prepared with reference to the nucleotide sequences represented by SEQ ID NO:1, 3 or 5 and genomic DNA of a microorganism having each of the genes as a template.

More specifically, the gene of the present invention can be obtained, for example by chemically synthesizing oligonucleotide A, which consists of a sequence containing N-terminal initiation codon of SLI1 gene represented by SEQ ID NO:1, and oligonucleotide B, which consists of a sequence complementary to a sequence containing a termination codon of the gene; and performing PCR using one set of these oligonucleotides A and B and genomic DNA of *Wickerhamomyces ciferrii* as a template. To efficiently clone the gene fragment thus obtained to a plasmid vector, etc., a sequence for restriction enzyme digestion can be added to the 5'-terminal of an oligonucleotide primer. As a primer herein, nucleotides chemically synthesized based on the information on the nucleotide sequence of SLI1 gene can be generally used; however, SLI1 gene already obtained or a fragment thereof can be satisfactorily used. Examples of the nucleotides include a partial nucleotide sequence corresponding to SEQ ID NO:1 and consisting of from 10 to 50 continuous bases, preferably from 15 to 35 continuous bases.

PCR conditions are, for example, 98° C. for 2 minutes, (98° C. for 10 seconds, 55° C. for 5 seconds, 72° C. for 1 minute)×30 cycles.

Furthermore, the gene of the present invention can be obtained by artificial synthesis by using a DNA synthesizer in accordance with the nucleotide sequence or amino acid sequence. In synthesizing DNA, another codon encoding the same amino acid residue may be selected in place of the codon originally used (codon conversion). An aspect of DNA obtained by the codon conversion includes DNA in which a codon present in DNA encoding SLI1 of *Wickerhamomyces ciferrii* but rare in a microorganism of the genus *Starmerella* (codon used less frequently in the microorganism) is converted into a codon encoding the same amino acid and highly frequently used in a translation mechanism of a microorganism in the genus *Starmerella*. More specifically, DNA consisting of the nucleotide sequence represented by SEQ ID NO:7 is mentioned. Similarly, as a DNA in which a codon present in DNA encoding SLI1 of *Saccharomyces cerevisiae* is converted to a codon encoding the same amino acid and highly frequently used in a *Starmerella* microorganism, DNA consisting of the nucleotide sequence represented by SEQ ID NO:8 is mentioned. Furthermore, as a DNA in which a codon present in DNA encoding SLI1 of *Pichia pastoris* is converted to a codon encoding the same amino acid and highly frequently used in a *Starmerella* microorganism, DNA consisting of the nucleotide sequence represented by SEQ ID NO:9 is mentioned.

In the present invention, introduction of an acetyltransferase gene into a microorganism of the genus *Starmerella* includes a method of introducing the acetyltransferase gene such that the gene can be expressed in the microorganism of the genus *Starmerella*.

The method for introducing the gene such that the gene can be expressed is not particularly limited. A nucleic acid fragment, which contains the acetyltransferase gene and is properly bound to a DNA fragment containing a transcription initiation regulatory region or a transcription initiation regulatory region and a ribosome binding site, upstream thereof, may be introduced.

Such a fragment can be genetically stably maintained in a host microorganism by (1) being directly introduced as a nucleic acid fragment, or introduced as a nucleic acid fragment in a plasmid vector, etc.; or by (2) being introduced as a nucleic acid fragment with partial genome sequences of the host organism at both ends for homologous recombination. The number of copies of the gene to be introduced is not particularly limited. In other words, a single copy and multiple copies of the gene may be introduced.

Examples of the method (1) of introducing a nucleic acid fragment into a host microorganism include an electroporation method and a lithium acetate method.

Furthermore, if the fragment is introduced in accordance with (2), homologous recombination takes place at the site corresponding to the sequence of the host chromosome, added to the nucleic acid fragment and the nucleic acid fragment introduced is integrated into the chromosome of the microorganism.

Note that the transcription initiation regulatory region or transcription initiation regulatory region and the ribosome binding site to bind to a site upstream the acetyltransferase gene are not particularly limited as long as they function in a host microorganism. As an example, the original transcription initiation regulatory region or transcription initiation regulatory region and ribosome binding site of the acetyltransferase gene, or another known transcription initiation regulatory region or transcription initiation regulatory region and ribosome binding site is mentioned. Alternatively, e.g., promoters of a glyceraldehyde-3-phosphate dehydrogenase gene, a cytochrome P450 monooxygenase and a UDP-glucosyltransferase gene can be used.

The target microorganism of the genus *Starmerella* to which the gene is to be introduced is not limited as long as the microorganism has a metabolic system producing a sphingoid base, at least sphingosine or phytosphingosine. Examples thereof include *Starmerella bombicola*, *Candida apicola* and *Candida floricola*. Among them, *Starmerella bombicola* is preferable. More specifically, e.g., *Starmerella bombicola* KSM36 strain (JP-A-61-31084) or NBRC10243 strain is mentioned. *Starmerella bombicola* is known to produce sophorolipid (SL) (Non Patent Literature 6) but incapable of producing an acetylated sphingoid base.

In the present invention, the acetylated sphingoid base refers to a compound obtained by substituting at least one of hydrogen atoms of an acetylatable group (a hydroxy group, an amino group, etc.) that a sphingoid base has with an acetyl group. Examples thereof include acetylated compounds of (2S,3S,4R)-2-aminooctadecane-1,3,4-triol (phytosphingosine), (2S,3R,4E)-2-amino-4-octadecene-1,3-diol (sphingosine), (2S,3R)-2-aminooctadecane-1,3-diol (sphinganine), (2S,3S,4R)-2-aminononadecane-1,3,4-triol (C19 phytosphingosine), (2S,3R,4E)-2-amino-4-nonadecene-1,3-diol (C19 sphingosine), (2S,3R)-2-aminononadecane-1,3-diol (C19 sphinganine), (2S,3S,4R)-2-aminoicosane-1,3,4-triol (C20 phytosphingosine), (2S,3R,4E)-2-amino-4-icosene-1,3-diol (C20 sphingosine) and (2S,3R)-2-aminoicosane-1,3-diol (C20 sphinganine). Among them, an acetylated sphingoid base obtained by substituting at least one of the hydroxyl group and amino group of a sphingoid base having a chain length of 19 or 20 carbon atoms with an acetyl group, is preferable. Among them, an acetylated phytosphingosine obtained by acetylating at least one of the hydroxyl group and amino group of a phytosphingosine having a chain length of 19 or 20 carbon atoms, is more preferable. Furthermore, an acetylated phytosphingosine obtained by acetylating at least one of the hydroxyl group and amino group of a phytosphingosine having a chain length of 20 carbon atoms, is even more preferable.

A microorganism thus prepared has an ability to produce an acetylated sphingoid base, and preferably an acetylated phytosphingosine having a chain length of 19 or 20 carbon atoms. The acetylated sphingoid base is accumulated in a culture medium when the microorganism is cultured.

An acetylated sphingoid base can be produced by culturing a microorganism according to the present invention as mentioned above in a medium, accumulating an acetylated sphingoid base in a culture solution and recovering the acetylated sphingoid base from the culture solution.

As described later in Examples, an acetylated sphingoid base having a chain length of 19 or 20 carbon atoms (for example, acetylated C19 phytosphingosine and acetylated C20 phytosphingosine) can be produced by using a microorganism of the present invention. Furthermore, the amount or ratio of an acetylated sphingoid base having a chain length of 19 carbon atoms produced can be increased by culturing the microorganism in a culture medium supplemented with a pentadecanoic acid alkyl ester, a heptadecanoic acid alkyl ester or a nonadecanoic acid alkyl ester. Furthermore, the ratio of an acetylated sphingoid base having a chain length of 20 carbon atoms produced can be increased by culturing the microorganism in a culture medium supplemented with an octadecanoic acid alkyl ester.

Herein, as an alkyl ester, an alkyl ester having from 1 to 4 carbon atoms is mentioned and preferably a methyl ester or ethyl ester is mentioned.

The amount of the fatty acid alkyl ester added is preferably 1 mass % or more and preferably 30 mass % or less, more preferably 10% or less, even more preferably 3% or less. In other words, the amount added is preferably from 1 to 30 mass %, more preferably from 1 to 10 mass %, even more preferably 1 to 3 mass %.

As the medium to be used for culture, a general medium containing a carbon source, a nitrogen source, inorganic salts, if necessary, organic micronutrients such as amino acids and vitamins can be used. Both a synthesis medium and a natural medium can be used. Any type of carbon source and nitrogen source may be used in a medium as long as a yeast strain to be cultured can utilize it.

As the carbon source, sugars such as glucose, glycerol, fructose, sucrose, maltose, mannose, galactose, starch hydrolysate and syrup can be used. Other than these, organic acids such as acetic acid and citric acid and alcohol such as ethanol can be used singly or in combination with another carbon source. As the nitrogen source, e.g., ammonia and an ammonium salt such as ammonium sulfate, ammonium carbonate, ammonium chloride, ammonium phosphate and ammonium acetate, or a nitrate can be used. As the organic micronutrient, e.g., amino acids, vitamins, fatty acids, nucleic acids; and peptone, casamino acid, a yeast extract and a soybean protein decomposition product containing these can be used. If an auxotrophic mutant requiring amino acids for growth is used, it is preferable to add the nutrients to be required. As the inorganic salts, e.g., a phosphate, a magnesium salt, a calcium salt, an iron salt and a manganese salt can be used.

Culture is preferably performed while controlling the culture temperature at from 20 to 35° C. If culture is performed under such conditions, preferably for about 24 hours to 120 hours, an acetylated sphingoid base can be accumulated in a culture solution.

After completion of culture, an acetylated sphingoid base is recovered from the culture solution. The recovering method is not particularly limited and recovering may be made in accordance with a known recovery method. An acetylated sphingoid base can be recovered, for example, by removing yeast cells from the culture solution, followed by applying a concentration crystallization method or column chromatograph.

Regarding the aforementioned embodiments, the following aspects are disclosed in the present invention.

<1> A method for producing an acetylated sphingoid base comprising culturing a microorganism of the genus *Starmerella* to which a xenogeneic gene encoding a polypeptide having an activity to acetylate a sphingoid base is introduced.

<2> The method for producing an acetylated sphingoid base according to <1>, in which the polypeptide having an activity to acetylate a sphingoid base consists of an amino acid sequence selected from the following (a) to (i):

(a) a polypeptide consisting of an amino acid sequence represented by SEQ ID NO:2, (b) a polypeptide consisting of an amino acid sequence which has a deletion, substitution or addition of one to several amino acid residues in the amino acid sequence represented by SEQ ID NO:2, (c) a polypeptide consisting of an amino acid sequence having a homology of 80% or more with the amino acid sequence represented by SEQ ID NO:2;

(d) a polypeptide consisting of an amino acid sequence represented by SEQ ID NO:4, (e) a polypeptide consisting of an amino acid sequence which has a deletion, substitution or addition of one to several amino acid residues in the amino acid sequence represented by SEQ ID NO:4, (f) a polypeptide consisting of an amino acid sequence having a homology of 80% or more with the amino acid sequence represented by SEQ ID NO:4;

(g) a polypeptide consisting of an amino acid sequence represented by SEQ ID NO:6, (h) a polypeptide consisting of an amino acid sequence which has a deletion, substitution or addition of one to several amino acid residues in the amino acid sequence represented by SEQ ID NO:6, and (i) a polypeptide consisting of an amino acid sequence having a homology of 80% or more with the amino acid sequence represented by SEQ ID NO:6.

<3> The method for producing an acetylated sphingoid base according to <2>, in which the one to several amino acids in (b), (e) and (h) means 1 to 80, preferably 1 to 40, more preferably 1 to 20, even more preferably 1 to 10 amino acids.

<4> The method for producing an acetylated sphingoid base according to <2>, in which the polypeptide (c) is an amino acid sequence having a homology of preferably 90% or more, more preferably 95% or more with the amino acid sequence of SEQ ID NO:2; the polypeptide (f) is an amino acid sequence having a homology of preferably 90% or more, more preferably 95% or more with the amino acid sequence of SEQ ID NO:4; and the polypeptide (i) is an amino acid sequence having a homology of preferably 90% or more, more preferably 95% or more with the amino acid sequence of SEQ ID NO:6.

<5> The method for producing an acetylated sphingoid base according to any one of <1> to <4>, in which the microorganism of the genus *Starmerella* is *Starmerella bombicola*.

<6> The method for producing an acetylated sphingoid base according to <5>, in which the *Starmerella bombicola* is *Starmerella bombicola* KSM36 strain or *Starmerella bombicola* NBRC10243 strain.

<7> The method for producing an acetylated sphingoid base according to any one of <1> to <6>, in which the acetylated sphingoid base is an acetylated phytosphingosine.

<8> The method for producing an acetylated sphingoid base according to any one of <1> to <7>, in which the acetylated sphingoid base is an acetylated sphingoid base having a chain length of 19 or 20 carbon atoms.

<9> The method for producing an acetylated sphingoid base according to <8>, in which the acetylated sphingoid base having a chain length of 19 or 20 carbon atoms is an acetylated phytosphingosine having a chain length of 19 or 20 carbon atoms.

<10> The method for producing an acetylated sphingoid base according to any one of <1> to <9>, in which at least one fatty acid alkyl ester selected from a pentadecanoic acid alkyl ester, a heptadecanoic acid alkyl ester, an octadecanoic acid alkyl ester and a nonadecanoic acid alkyl ester is added to a culture medium.

<11> The method for producing an acetylated sphingoid base according to <10>, in which the fatty acid alkyl ester is an ester of an alkyl having 1 to 4 carbon atoms and a fatty acid.

<12> The method for producing an acetylated sphingoid base according to <10> or <11>, in which an amount of the fatty acid alkyl ester added to the medium is preferably from 1 to 30 mass %, more preferably from 1 to 10 mass %, even more preferably from 1 to 3 mass %.

<13> A microorganism in the genus *Starmerella* to which a xenogeneic gene encoding a polypeptide having an activity to acetylate a sphingoid base is introduced.

<14> The microorganism in the genus *Starmerella* according to <13>, in which the polypeptide having an activity to acetylate a sphingoid base consists of an amino acid sequence selected from the following (a) to (i):

(a) a polypeptide consisting of an amino acid sequence represented by SEQ ID NO:2, (b) a polypeptide consisting of an amino acid sequence which has a deletion, substitution or addition of one to several amino acid residues in the amino acid sequence represented by SEQ ID NO:2, (c) a polypeptide consisting of an amino acid sequence having a homology of 80% or more with the amino acid sequence represented by SEQ ID NO:2;

(d) a polypeptide consisting of an amino acid sequence represented by SEQ ID NO:4, (e) a polypeptide consisting of an amino acid sequence which has a deletion, substitution or addition of one to several amino acid residues in the amino acid sequence represented by SEQ ID NO:4, (f) a polypeptide consisting of an amino acid sequence having a homology of 80% or more with the amino acid sequence represented by SEQ ID NO:4;

(g) a polypeptide consisting of an amino acid sequence represented by SEQ ID NO:6, (h) a polypeptide consisting of an amino acid sequence which has a deletion, substitution or addition of one to several amino acid residues in the amino acid sequence represented by SEQ ID NO:6, (i) a polypeptide consisting of an amino acid sequence having a homology of 80% or more with the amino acid sequence represented by SEQ ID NO:6.

<15> The microorganism in the genus *Starmerella* according to <14>, in which the one to several amino acids in (b), (e) and (h) means 1 to 80, preferably 1 to 40, more preferably 1 to 20, even more preferably 1 to 10.

<16> The microorganism in the genus *Starmerella* according to <14>, in which the polypeptide (c) is an amino acid sequence having a homology of preferably 90% or more, more preferably 95% or more with the amino acid sequence of SEQ ID NO:2; the polypeptide (f) is an amino acid sequence having a homology of preferably 90% or more, more preferably 95% or more with the amino acid sequence of SEQ ID NO:4; and the polypeptide (i) is an amino acid sequence having a homology of preferably 90% or more, more preferably 95% or more with the amino acid sequence of SEQ ID NO:6.

<17> The microorganism in the genus *Starmerella* according to any one of <13> to <16>, in which the microorganism in the genus *Starmerella* is *Starmerella bombicola*.

<18> The *Starmerella* microorganism according to <17>, in which the *Starmerella bombicola* is *Starmerella bombicola* KSM36 strain or *Starmerella bombicola* NBRC10243 strain.

The content of the present invention will be described more specifically by way of the following Examples.

EXAMPLES

Example 1: Preparation of a Strain Having WcSLI1 Gene Derived from *Wickerhamomyces ciferrii* Introduced Therein (1) Construction of Gene Fragment to be Introduced Acetyltransferase gene (WcSLI1) (SEQ ID NO:7) derived from *Wickerhamomyces ciferrii* was artificially synthesized in accordance with codon usage of *Starmerella bombicola*. Then, PCR was performed using the acetyltransferase gene (WcSLI1) as a template and primers of SEQ ID NOs:10 and 12 or primers of SEQ ID NOs:11 and 12 to obtain a WcSLI1 gene fragment. The conditions of PCR are, for example, 98° C. for 2 minutes, (98° C. for 10 seconds, 55° C. for 5 seconds, 72° C. for 1 minute)×30 cycles. For expression of WcSLI1, a promoter of Glyceraldehyde-3-phosphate dehydrogenase (5'-GAPDH) and a promoter of UDP-glucosyltransferase (5'-UGT) gene were used. Individual promoter sequences were obtained by PCR using primers of SEQ ID NOs:13 and 14 and primers of SEQ ID NOs:15 and 16 and using genomic DNA of *Starmerella bombicola* KSM36 strain as a template. In addition, a terminator of Cytochrome C (3'-CYC) was used. The sequence of 3'-CYC was obtained by PCR using primers of SEQ ID NOs:17 and 18 and genomic DNA of *Starmerella bombicola* KSM36 strain as a template. These were ligated by use of SOE-PCR to obtain [5'-GAPDH or 5'-UGT] [WcSLI1][3'-CYC] gene fragment. The gene fragment and plasmid pHsp70A/RbcS2-Chlamy (Chlamydomonas Resource Center) were treated with restriction enzymes SacI and NcoI and ligated by use of in-Fusion cloning kit (Clontech) to obtain plasmid 1. A transformant was screened by use of a hygromycin resistant gene (SEQ ID NO:19). The hygromycin resistant gene was obtained by PCR using primers of SEQ ID NOs:20 and 21 and plasmid loxP-PGK-gb2-hygro-loxP (Gene Bridges) having a hygromycin resistant gene as a template, and then, a promoter and a terminator of URA3 gene were separately amplified by PCR using genomic DNA of *Starmerella bombicola* KSM36 strain as a template and primers of SEQ ID NOs:22 and 23 or 24 and 25. The hygromycin resistant gene was ligated with the products thus amplified by means of SOE-PCR to obtain a gene fragment [5'-URA 3] [hygromycin resistant gene] [3'-URA3]. Furthermore, plasmid pUC-Arg7-lox-B ARG7 was subjected to PCR with primers of SEQ ID NOs:26 and 27 to amplify the region except ARG7, which was ligated with amplified product by SOE-PCR by use of in-Fusion cloning kit (Clontech) to obtain plasmid 2. Ligation was performed using loxP sequences of plasmid 1 and plasmid 2 by a cre recombinase reaction to obtain a sequence of [5'-GAPDH or 5'-UGT] [WcSLI1] [3'-CYC]-[5'-URA3] [hygromycin resistant gene] [3'-URA3] as plasmid 3. Plasmid 3 was subjected to PCR using primers of SEQ ID NOs:13 and 25 or 15 and 25 to obtain a WcSLI1-introduced gene fragment.

Furthermore, a gene fragment to be introduced for deleting cyp52M1, was prepared as follows. The upstream region of cyp52M1 gene was amplified by PCR using primers of SEQ ID NOs:28 and 29; the downstream region thereof by PCR using primers of SEQ ID Nos:30 and 31; and URA3 gene by using primers of SEQ ID Nos:32 and 33, using genomic DNA of *Starmerella bombicola* KSM36 strain as a template. The three fragments thus obtained were ligated by SOE-PCR. The resultant fragment was used as a cyp52M1 deficient fragment.

The primers used in Example 1 are summarized in Table 1.

TABLE 1

| SEQ ID NO | Primer Name | Sequence (5' → 3') |
|---|---|---|
| 10 | pGAPDH-WcSLI1-Fw | CAACTCTACACAAATGGTGGCTGGGCCGAACAAG |
| 11 | pUGT-WcSLI1-Fw | CTACGAATATTCAATGGTGGCTGGGCCGAACAAG |
| 12 | WcSLI1-Rv | GAGTGAGCTGTCATTCATAATACCCATTGATAG |
| 13 | pGAPDH-Fw | CATCCGATGTGTAGTTAATCATTG |
| 14 | pGAPDH-Rv | TTGTGTAGAGTTGTTTTTGTTG |
| 15 | pUGT-Fw | CAAACCTGATCTTTAGTGAACTG |
| 16 | pUGT-Rv | TGAATATTCGTAGGGAGAAGC |
| 17 | tCYC-Fw | AGCTCACTCGTTGAGAGAGCAC |
| 18 | tCYC-Rv | CGACAGGTCATGTTATCAAGCCGAG |
| 20 | Hyg-Fw | CACTACTGTAGAGAAATAATATGAAAAAGCCTGAACTCAC |
| 21 | Hyg-Rv | CATTGAAGGAACTGTTTGAGAAAACTATTCCTTTGCCCTCGGACGAG |
| 22 | pURA3-Fw | TTAAGATCTCAGCTTTTTCGAAACAGCTCGCAACGATC |
| 23 | pURA3-Rv | GTGAGTTCAGGCTTTTTCATATTATTTCTCTACAGTAGTG |

TABLE 1-continued

| SEQ ID NO: | Primer Name | Sequence (5' → 3') |
|---|---|---|
| 24 | tURA3-Fw | CTCGTCCGAGGGCAAAGGAATAGTTTTCTCAAACAGTTCCTTCAATG |
| 25 | tURA3-Rv | CGATATCTTCGTCTTCATCATCGTCACTATACACATC |
| 26 | pUClox-Fw | TCGACTCTAGAATTCATAACTTC |
| 27 | pUClox-Rv | ACGAAGATATCGTACCGATC |
| 28 | CYP52M1 (1)-Fw | ACAAATCCAGCCAGCGGGTTTG |
| 29 | CYP52M1 (1)-Rv | ATATGTACTTTTCAATATGATAAAC |
| 30 | CYP52M1 (2)-Fw | GTTTCTTAGCCTCCCATGGAAG |
| 31 | CYP52M1 (2)-Rv | CGGAGAAAATTGTTCGATGGATAG |
| 32 | URA3-Fw | TATTGAAAAGTACATATTTTTCGAAACAGCTCGCAACGATC |
| 33 | URA3-Rv | GGGAGGCTAAGAAACTTCATCATCGTCACTATACACATC |

(2) Acquisition of Uracil Auxotrophic Strain

*Starmerella bombicola* KSM36 strain (FERM BP-799) was inoculated into SD-U agar medium containing 0.68% Yeast Nitrogen Base w/o amino acids, 2% glucose, 0.03% uracil and 1.5% Agar and then cultured at 30° C. for one month. The obtained yeast cells were taken by a platinum loop and suspended in 1 mL of 0.8% saline solution. 100 μL of the suspension was spread on SD-UF agar medium containing 0.68% Yeast Nitrogen Base w/o amino acids, 2% glucose, 0.03% uracil, 5-fluoroorotic acid and 1.5% Agar and cultured at 30° C. for 2 weeks. The grown colonies were cultured again in SD-UF agar medium. Thereafter, cultured products were each confirmed for uracil auxotrophy and 5-fluoroorotic acid resistance, and then, an uracil auxotrophic strain was obtained.

*Starmerella bombicola* KSM36 strain and the obtained uracil auxotrophic strain were each taken by a platinum loop and inoculated into 5 mL of 50 g/L YPD Broth (manufactured by Japan BD) contained in a 100-mL volume test tube and cultured at 30° C. and 250 rpm for 48 hours. The culture solution (1 mL) was centrifuged at 5000 rpm at 4° C. for 5 minutes to collect yeast cells. From the yeast cells, genomic DNA was extracted by using Dr.GenTLE™ (TAKARA Bio) in accordance with the method described in the attached instruction. Using primers (SEQ ID. NOs:32, 33) listed in Table 1 and KOD-plus. ver 2 (TOYOBO), URA3 gene encoding orotidine decarboxylase involved in uracil biosynthesis was amplified. Sequence of the URA3 gene was analyzed using the PCR product as a template and compared to the sequence of *Starmerella bombicola* NBRC10243 strain (GenBank accession No. DQ916828). As the result, it was confirmed that *Starmerella bombicola* KSM36 strain has the same sequence as that of the URA gene of *Starmerella bombicola* NBRC10243 strain; the uracil auxotrophic strains all have a mutation (cysteine is changed to tyrosine) at the 54-position. The obtained uracil auxotrophic strain was used as *Starmerella bombicola* KSM36-ura3 strain.

(3) Acquisition Method for Uracil Auxotrophic Strain

Since the mutation position of the uracil auxotrophic strain was determined in the section (2), it became possible to easily prepare an uracil auxotrophic strain, for example, by using the following gene recombinant means.

URA3 gene was amplified using genomic DNA of *Starmerella bombicola* KSM36 strain as a template and primers of SEQ ID NOs:32 and 33. The amplified gene fragment was introduced into an appropriate vector to introduce a point mutation for changing cysteine at the 54-position to tyrosine. The vector to which a point mutation was introduced was amplified by using the primers of SEQ ID NOs:32 and 33 to obtain a transformed fragment containing the mutation introduced in URA3 gene. *Starmerella bombicola* KSM36 was taken by a platinum loop, inoculated into YPD Broth (5 mL) contained in a 100 mL-volume test tube and cultured at 30° C. and 250 rpm for 24 hours. The obtained culture solution was inoculated so as to obtain a concentration of 1% in YPD Broth (50 mL) contained in a Sakaguchi flask and cultured at 30° C. and 120 rpm until OD600 reaches 1 to 2. The yeast cells proliferated were collected by centrifugation at 3000 rpm and 4° C. for 5 minutes and washed twice with ice-cooled sterilized water (20 mL). The yeast cells were suspended in 1 mL of an ice-cooled 1M sorbitol solution and centrifuged at 5000 rpm and 4° C. for 5 minutes. After the supernatant was discarded, 400 μL of a 1M sorbitol solution was added. The mixture was allowed to stand on ice and suspended by pipetting. The yeast suspension solution (50 μL) was taken and dispensed, and DNA (1 μg) for transformation was added. The yeast suspension solution was transferred to an ice-cooled chamber having a gap of 0.2 cm (BIO-RAD) and thereafter, a pulse (25 μF, 350Ω, 2.5 kV) was applied by use of GENE PULSER II (BIO-RAD). An ice-cooled 1M sorbitol-containing YPD Broth was added and the mixture was transferred to a 1.5 mL-volume tube, shaken at 30° C. for 2 hours and then centrifuged at 5000 rpm and 4° C. for 5 minutes to recover the yeast cells. The yeast cells were resuspended in 200 μL of a 1M sorbitol solution. An aliquot (100 μL) was taken, spread on a selective medium and cultured at 30° C. for about one week. As the selective medium, SD-UF agar medium containing 0.68% Yeast Nitrogen Base w/o amino acids, 2% glucose, 0.03% uracil, 5-fluoroorotic acid and 1.5% Agar was used. The colonies grown were cultured again in the SD-UF agar medium. Thereafter, the cultured products were each confirmed for uracil auxotrophy and 5-fluoroorotic acid resistance. In this manner, a uracil auxotrophic strain could be obtained.

(4) Acquisition of cyp52M1 Gene Deficient Strain

*Starmerella bombicola* KSM36-ura3 strain obtained above was taken by a platinum loop, inoculated into YPD Broth (5 mL) contained in a 100 mL-volume test tube and cultured at 30° C. and 250 rpm for 24 hours. The obtained culture solution was inoculated so as to obtain a concentration of 1% in YPD Broth (50 mL) contained in a Sakaguchi flask and cultured at 30° C. and 120 rpm until OD600 reached 1 to 2. The yeast cells proliferated were collected by centrifugation at 3000 rpm and 4° C. for 1 minute and washed twice with ice-cooled sterilized water (20 mL). The yeast cells were suspended in 1 mL of an ice-cooled 1M sorbitol solution and centrifuged at 5000 rpm and 4° C. for 5 minutes. After the supernatant was discarded, 400 µL of a 1M sorbitol solution was added. The mixture was allowed to stand on ice and suspended by pipetting. The yeast suspension solution (50 µL) was taken and dispensed, and 1 µg of DNA (cyp52M1 deficient gene fragment) for transformation was added. The yeast suspension solution was transferred to an ice-cooled chamber having a gap of 0.2 cm (BIO-RAD) and thereafter, a pulse (25 µF, 350Ω, 2.5 kV) was applied by use of GENE PULSER II (BIO-RAD). An ice-cooled 1M sorbitol-containing YPD Broth was added and the mixture was transferred to a 1.5 mL-volume tube, shaken at 30° C. for 2 hours and then centrifuged at 5000 rpm and 4° C. for one minute to recover yeast cells. The yeast cells were resuspended in 200 µL of a 1M sorbitol solution. An aliquot (100 µL) was taken, spread on a selective medium and cultured at 30° C. for about one week. As the selective medium, SD-ura agar medium containing 0.68% Yeast Nitrogen Base w/o Amino Acids, 2% glucose, 0.077% CSM-ura (Funakoshi) and 1.5% Agar was used. The colonies grown were subjected to colony PCR using primers of SEQ ID NOs:28 and 31 by KOD-FX-Neo (TOYOBO). After confirming that the length of the sequence amplified was changed, cyp52M1 gene deficient strain was obtained.

(5) Introduction of WcSLI1 Gene into *Starmerella bombicola*

*Starmerella bombicola* cyp52M1 gene deficient strain and *Starmerella bombicola* KSM36 strain were each taken by a platinum loop, inoculated into YPD Broth (5 mL) contained in a 100 mL-volume test tube and cultured at 30° C. and 250 rpm for 24 hours. The culture solution obtained was inoculated so as to obtain a concentration of 1% in YPD Broth (50 mL) contained in a Sakaguchi flask and cultured at 30° C. and 120 rpm until OD600 nm reached 1 to 2. The yeast cells proliferated were collected by centrifugation at 3000 rpm and 4° C. for 5 minutes and washed twice with ice-cooled sterilized water (20 mL). The yeast cells were suspended in 1 mL of an ice-cooled 1M sorbitol solution and centrifuged at 5000 rpm and 4° C. for one minute. After the supernatant was discarded, 400 µL of a 1M sorbitol solution was added. The mixture was allowed to stand on ice and suspended by pipetting. The yeast suspension solution (50 µL) was taken and dispensed, and 1 µg of DNA (WcSLI1 introduced gene fragment) for transformation was added. The yeast suspension solution was transferred to an ice-cooled chamber having a gap of 0.2 cm (BIO-RAD) and thereafter, a pulse (25 µF, 350Ω, 2.5 kV) was applied by use of GENE PULSER II (BIO-RAD). An ice-cooled 1M sorbitol-containing YPD Broth was added and the mixture was transferred to a 1.5 mL-volume tube, shaken at 30° C. for 2 hours, and then centrifuged at 5000 rpm and 4° C. for one minute. The yeast cells were recovered and resuspended in 200 µL of a 1M sorbitol solution. An aliquot (100 µL) was taken, spread on a selective medium and cultured at 30° C. for about one week. As the selective medium, SD-ura+hygromycin agar medium containing 0.68% Yeast Nitrogen Base w/o Amino Acids, 2% glucose, 0.077% CSM-ura (Funakoshi), 200 µg/mL hygromycin and 1.5% Agar was used. The colonies grown were subjected to colony PCR using primers of SEQ ID NOs:13 and 18 or 15 and 18 by KOD-FX-Neo (TOYOBO). After confirming that the gene was inserted in the genome, Δcyp52M1/pGAPDH-WcSLI1 strain (GAPDH promoter was used) and Δcyp52M1/pUGT-WcSLI1 strain (UGT promoter was used) having the gene introduced in *Starmerella bombicola* cyp52M1 deficient strain; and pGAPDH-WcSLI1 strain and pUGT-WcSLI1 strain having the gene introduced in *Starmerella bombicola* KSM36 strain, were obtained. Furthermore, as a control, a strain having the hygromycin resistant gene alone introduced therein was obtained.

Example 2: Analysis of Acetylated Phytosphingosine Productibility in Strain Having WcSLI1 Gene Introduced Therein (1)

(1) Analysis of Lipid Composition of the Strain Having the Gene Introduced Therein A control strain (hygromycin resistant gene), Δcyp52M1pGAPDH-WcSLI1 strain and Δcyp52M1/pUGT-WcSLI1 strain were each spread on YPD agar medium. The colonies grown were taken by a platinum loop, inoculated into SD-Ura medium (5 mL) contained in a 100 mL-volume test tube and cultured at 30° C. and 250 rpm for 24 hours. The obtained culture solution (500 µL) was inoculated into SD-Ura medium (5 mL) contained in a 100 mL-volume test tube and cultured at 30° C. and 250 rpm for 24 to 72 hours. Then, lipid composition was analyzed.

(2) Quantification of Acetylated Phytosphingosine

After the culture solution (1 mL) was recovered, 4 mL of a solution mixture containing chloroform and methanol in a ratio of 2:1 was added, vortexed and then allowed to stand still for 15 min. The mixture was centrifuged at 3000 rpm for 15 minutes and the lower layer (chloroform layer) was collected. The solution collected was dried by blowing nitrogen gas, suspended in 1 mL of methanol, appropriately diluted and filtered through a filter. After filtration, the sample was measured by LC-MS/MS. The conditions of LC-MS/MS are as follows:

LC conditions: Capcell core C18 2.7 µmφ 2.1×50 mm (Shiseido Co., Ltd.), Oven Temp. 40° C., Sol. A: 0.1% $HCO_2H$ in water, Sol. B: MECN, (A60%, B40%) 0.5 min→[(A60%, B40%)→(A0%, B100%) 5.5 min]→B100% 2 min, [(A0%, B100%)→(A60%, B40%) 0.01 min]→ (A60%, B40%) 2 min, Flow rate 0.6 ml/min., Inject 5 µL, MS/MS apparatus: API3200QTrap (AB SCIEX).

TABLE 2

| Ions used for quantification of acetylated phytosphingosines | | | |
|---|---|---|---|
| | Precursor ion/Product ion(m/z) The length of carbon chain of phytosphingosine | | |
| | C18 | C19 | C20 |
| Monoacetylated phytosphingosine | 360.4/264.4 | 374.4/278.3 | 388.4/292.3 |
| Triacetylated phytosphingosine | 444.3/264.4 | 458.3/278.3 | 472.3/292.3 |
| Tetraacetylated phytosphingosine | 486.4/264.4 | 500.4/278.3 | 514.4/292.3 |

Lipid compositions after culture for 24 and 48 hours were shown in FIG. 1. In the control strain, neither triacetylphytosphingosine (TriAPS) (length of carbon chain: 18) nor tetraacetylphytosphingosine (TAPS) (length of carbon chain: 18) were produced; whereas, in *Starmerella bombicola* having WcSLI1 gene introduced therein, production of TriAPS and TAPS were confirmed.

The amounts of acetylated phytosphingosines produced at 72nd hour after initiation of culture and the ratios of the products are shown in Table 3 and Table 4.

TABLE 3

Amounts of triacetylated phytosphingosines having a chain length of from 18 to 20 carbon atoms produced and the ratios of the products

| | Amount produced | Ratio(%) | | |
|---|---|---|---|---|
| | (mg/L) | C18 | C19 | C20 |
| Control strain | n.d. | — | — | — |
| pGAPDH-SLI1 strain | 23.3 | 22.5 | 7.5 | 70.0 |
| pUGT-SLI1 strain | 17.7 | 17.8 | 11.2 | 70.9 |

TABLE 4

Amounts of tetraacetylated phytosphingosines having a chain length of from 18 to 20 carbon atoms produced and the ratios of the products

| | Amount produced | Ratio(%) | | |
|---|---|---|---|---|
| | (mg/L) | C18 | C19 | C20 |
| Control strain | n.d. | — | — | — |
| pGAPDH-SLI1 strain | 0.11 | 16.2 | 9.6 | 74.2 |
| pUGT-SLI1 strain | 0.06 | 14.9 | 17.3 | 67.8 |

Example 3: Analysis of Acetylated Phytosphingosines Productibility in Strain Having WcSLI1 Gene Introduced Therein (2)

Δcyp52M1/pGAPDH-WcSLI1 strain was spread on YPD agar medium. The colonies grown were taken by a platinum loop, inoculated into SD-Ura medium (5 mL) contained in a 100 mL-volume test tube and cultured at 30° C. and 250 rpm for 24 hours. The obtained culture solution (100 μL) was inoculated into SD-Ura medium (5 mL) with a C15 to C19 fatty acid ethyl ester (50 mM) contained in a 100 mL-volume test tube and cultured at 30° C. and 250 rpm for 72 hours. Then, lipid composition was analyzed in the same manner as in Example 2.

The amounts of C18 to C20 acetylated phytosphingosines produced at 72nd hour after initiation of culture and the ratios of the products are shown in Table 5 and Table 6

TABLE 5

Amounts of triacetylated phytosphingosines having a chain length of 18 to 20 carbon atoms produced and the ratios of the products

| | Amount produced | Ratio(%) | | |
|---|---|---|---|---|
| | (mg/L) | C18 | C19 | C20 |
| No additives | 23.3 | 22.5 | 7.5 | 70.0 |
| Ethyl pentadecanoate | 18.4 | 0.6 | 94.4 | 5.0 |
| Ethyl hexadecanoate | 19.9 | 52.7 | 3.6 | 43.6 |
| Ethyl heptadecanoate | 27.7 | 0.4 | 97.0 | 2.7 |
| Ethyl stearate | 22.6 | 4.3 | 2.3 | 93.4 |
| Ethyl nonadecanoate | 28.7 | 6.2 | 68.6 | 25.2 |

TABLE 6

Amounts of tetraacetylated phytosphingosines having a chain length of from 18 to 20 carbon atoms produced and the ratios of the products

| | Amount produced | Ratio(%) | | |
|---|---|---|---|---|
| | (mg/L) | C18 | C19 | C20 |
| No additives | 0.11 | 16.2 | 9.6 | 74.2 |
| Ethyl pentadecanoate | 0.12 | 1.1 | 95.4 | 3.5 |
| Ethyl hexadecanoate | 0.05 | 80.6 | 2.1 | 17.3 |
| Ethyl heptadecanoate | 0.12 | 0.5 | 97.5 | 2.0 |
| Ethyl stearate | 0.05 | 4.9 | 3.0 | 92.2 |
| Ethyl nonadecanoate | 0.14 | 4.0 | 84.5 | 11.5 |

Reference Example: Analysis of Acetylated Phytosphingosine Productibility in Strain Having WcSLI1 Gene Introduced Therein (3)

Δcyp52M1/pGAPDH-WcSLI1 strain, pGAPDH-WcSLI1 strain, Δcyp52M1/pUGT-WcSLI1 strain and pUGT-WcSLI1 strain were each spread on YPD agar medium. The colonies grown were taken by a platinum loop, inoculated into YPD medium (5 mL) contained in a 100 mL-volume test tube and cultured at 30° C. and 250 rpm for 24 hours. The obtained culture solution (100 μL) was inoculated into modified YPD medium (10% glucose, 10% ethyl hexadecanoate, 2% Peptone, 1% Yeast Extract, 25 mM $CaCl_2.2H_2O$, 50 mM L-serine) (5 mL) contained in a 100 mL-volume test tube, and cultured at 30° C. and 250 rpm for 7 days. Then, lipid composition was analyzed in the same manner as in Example 2. The results of lipid analysis are shown in Table 7. Furthermore, fatty acid ethyl ester or fatty acid was extracted from the culture solution (1 mL) by using 2 mL of hexane. After the hexane layer was collected, ethyl acetate (2 mL) was added to the remaining water layer to extract sophorolipid and the ethyl acetate layer was collected. The ethyl acetate layer was dried and analyzed. As the result, it was confirmed that Δcyp52M1/pGAPDH-WcSLI1 strain and Δcyp52M1/pUGT-WcSLI1 strain produced no sophorolipid; whereas, pGAPDH-WcSLI1 strain and pUGT-WcSLI1 strain produced sophorolipid.

TABLE 7

Amounts of triacetylated phytosphingosines having a chain length of 18 to 20 carbon atoms produced and the ratios of the products

| | Amount produced | Ratio(%) | | |
|---|---|---|---|---|
| | (mg/L) | C18 | C19 | C20 |
| Δcyp52M1/pGAPDH-WcSLI1 strain | 34.4 | 71.7 | 2.3 | 26.1 |
| Δcyp52M1/pUGT-WcSLI1 strain | 39.1 | 73.5 | 2.1 | 24.4 |
| pGAPDH-WcSLI1 strain | 71.1 | 44.6 | 3.2 | 52.2 |
| pUGT-WcSLI1 strain | 68.1 | 51.1 | 3.1 | 45.8 |

Example 4: Preparation of Strain Having Various Xenogeneic SLI1 Introduced (1) Preparation of a Fragment for Introduction An upstream site of CYP52M1 gene was amplified by PCR using primers of SEQ ID NOs:34 and 35 and genomic DNA of *Starmerella bombicola* KSM36 strain as a template and ligated with plasmid 1, which was obtained by amplification using primers of SEQ ID NOs:36 and 37, by use of in-Fusion cloning kit (Clontech) to insert the upstream site of CYP52M1 gene ahead of the GAPDH promoter. This was designated as plasmid 1-A. Subsequently, a region containing a promoter and a terminator of URA3 gene was amplified by PCR using primers of SEQ ID NOs:22 and 25 and genomic DNA of *Starmerella bombicola* KSM36 strain as a template. Furthermore, the region except ARG7 of plasmid pUC-Arg7-lox-B ARG7 was amplified using primers of SEQ ID NOs:26 and 27 and ligated with the amplification product of URA3, by use of in-Fusion cloning kit (Clontech). The obtained plasmid was designated as plasmid 2-A. Furthermore, a downstream site of CYP52M1 gene was amplified by PCR using primers of SEQ ID NOs:38 and 39 and genomic DNA of *Starmerella bombicola* KSM36 strain as a template and ligated with plasmid 2-A which was obtained by amplification using primers of SEQ ID NOs:40 and 41, by use of in-Fusion cloning kit (Clontech) to insert the downstream site of CYP52M1 gene backward into the URA3 terminator. This was designated as plasmid 2-B. Plasmid 1-A and Plasmid 2-B were ligated by Cre recombinase reaction to obtain a plasmid 4. PCR was performed using primers of SEQ ID NOs:28 and 31 and plasmid 4 as a template to obtain cyp52M1::pGAPDH-WcSLI1 fragment.

(2) Preparation of Fragment for Introducing Xenogeneic SLI1

SLI1 genes derived from *Saccharomyces cerevisiae* and *Pichia pastoris* were artificially synthesized in accordance with codon usage of *Starmerella bombicola* to obtain sequences represented by SEQ ID NOs:8 and 9, respectively. Using these as templates and primers of SEQ ID NOs:42, 43 and 44, 45, PCR was performed to obtain ScSLI1 and PpSLI1 fragments. Subsequently, using primers of SEQ ID NOs:46 and 47 and plasmid 4 as a template, PCR was performed to amplify the region except WcSLI1. The ScSLI1 fragment and PpSLI1 fragment were ligated with a plasmid by use of in-Fusion cloning kit (Clontech) to obtain plasmids 5 and 6, respectively. Using primers of SEQ ID NOs:28 and 31 and plasmids 5 or 6 as a template, PCR was performed to obtain cyp52M1::pGAPDH-ScSLI1 fragment and cyp52M1::pGAPDH-PpSLI1 fragment.

(3) Preparation of Various SLI1-Introduced Strains

*Starmerella bombicola* KSM36-ura3 strain as mentioned above was taken by a platinum loop and inoculated into YPD Broth (5 mL) contained in a 100 mL-volume test tube and cultured at 30° C. and 250 rpm for 24 hours. The culture solution obtained was inoculated so as to obtain a concentration of 1% in YPD Broth (50 mL) contained in a Sakaguchi flask, and cultured at 30° C. and 120 rpm until OD600 reached 1 to 2. The yeast cells proliferated were collected by centrifugation at 3000 rpm and 4° C. for 5 minutes and washed twice with ice-cooled sterilized water (20 mL). The yeast cells were suspended in 1 mL of an ice-cooled 1M sorbitol solution and centrifuged at 5000 rpm and 4° C. for one minute. After the supernatant was discarded, 400 μL of a 1M sorbitol solution was added. The resultant mixture was placed on ice and suspended by pipetting. The yeast suspension solution (50 μL) was taken and dispensed, and 1 μg of DNA for transformation was added. The yeast suspension solution was transferred to an ice-cooled chamber having a gap of 0.2 cm (BIO-RAD), and thereafter, a pulse (25 μF, 350Ω, 2.5 kV) was applied by use of GENE PULSER II (BIO-RAD). An ice-cooled 1M sorbitol-containing YPD Broth was added and the mixture was transferred to a 1.5 mL-volume tube, shaken at 30° C. for 2 hours and then centrifuged at 5000 rpm and 4° C. for one minute. The yeast cells were recovered and resuspended in 200 μL of a 1M sorbitol solution. An aliquot (100 μL) was taken, spread on a selective medium and cultured at 30° C. for about one week. As the selective medium, SD-ura agar medium containing 0.68% Yeast Nitrogen Base w/o Amino Acids, 2% glucose, 0.077% CSM-ura (Funakoshi) and 1.5% Agar was used. The colonies grown were subjected to colony PCR using primers of SEQ ID NOs:28 and 31 by KOD-FX-Neo (TOYOBO). After confirming that the length of the sequence amplified changed, cyp52M1::pGAPDH-WcSLI1 strain, cyp52M1::pGAPDH-ScSLI1 strain and cyp52M1::pGAPDH-PpSLI1 strain were obtained. The primers used in Example 4 are summarized in Table 8.

TABLE 8

| SEQ ID NO: | Primer Name | Sequence (5' → 3') |
|---|---|---|
| 34 | CYP52M1 (1)-1-Fw | CTGATAGCGAGCTCACAAATCCAGCCAGCGGGTTTG |
| 35 | CYP52M1 (1)-1-Rv | ACTACACATCGGATGATATGTACTTTTCAATATGATAAAC |
| 36 | Plasmid 1-Fw | GAGCTCGCTATCAGCCTCGACT |
| 37 | Plasmid 1-Rv | CATCCGATGTGTAGTTAATCATTG |
| 38 | CYP52M1 (2)-1-Fw | GTGACGATGATGAAGTTTCTTAGCCTCCCATGGAAG |
| 39 | CYP52M1 (2)-1-Rv | CGATATCTTCGTCCGGAGAAAATTGTTCGATGGATAG |
| 40 | Plasmid 2A-Fw | TTCATCATCGTCACTATACACATC |
| 41 | Plasmid 2A-Rv | GACGAAGATATACGTACCGAT |
| 42 | ScSLI1-Fw | ACAAAAACAACTCTACACAAATGAATCTCAAGCTGTCCGC |
| 43 | ScSLI1-Rv | TCTCTCTCAACGAGTGAGCTTCAGTACAAATTAAGATAGTCC |
| 44 | PpSLI1-Fw | ACAAAAACAACTCTACACAAATGGAAGGCACTACAAGCCAAG |
| 45 | PpSLI1-Rv | TCTCTCTCAACGAGTGAGCTTCAGATGTCTCTAATAAACTC |
| 46 | Plasmid 4-Fw | TTGTGTAGAGTTGTTTTTGTTG |
| 47 | Plasmid 4-Rv | AGCTCACTCGTTGAGAGAGAGCAC |

Example 5: Evaluation of Acetylated Phytosphingosine Productibility of Various SLI1 Expressing Strains Three strains obtained in Example 4 and cyp52M1 deficient strain were each spread on YPD agar medium. The colonies grown were taken by a platinum loop and inoculated into SD-Ura medium (5 mL) contained in a 100 mL-volume test tube and cultured at 30° C. and 250 rpm for 24 hours. The obtained culture solution (100 μL) was inoculated into SD-Ura medium (5 mL) contained in a 100 mL-volume test tube and cultured at 30° C. and 250 rpm for 120 hours. Then, lipid composition was analyzed in the same manner as in Example 2. The amount of C18 to C20 acetylated phytosphingosine produced at 120th hour after initiation of culture and the ratio of the products are shown in Table 9 and Table 10.

TABLE 9

Amounts of monoacetylated phytosphingosines having a chain length of 18 to 20 carbon atoms produced and the ratios of the products

| | Amount produced (mg/L) | Ratio(%) C18 | C19 | C20 |
|---|---|---|---|---|
| cyp52M1 deficient strain | n.d. | — | — | — |
| cyp52M1::pGAPDH-WcSLI1 strain | 0.05 | 0 | 0 | 100 |
| cyp52M1::pGAPDH-ScSLI1 strain | 0.47 | 0 | 16.2 | 83.8 |
| cyp52M1::pGAPDH-PpSLI1 strain | 0.43 | 8.0 | 15.0 | 76.9 |

TABLE 10

Amounts of triacetylated phytosphingosines having a chain length of 18 to 20 carbon atoms produced and the ratios of the products

| | Amount produced (mg/L) | Ratio(%) C18 | C19 | C20 |
|---|---|---|---|---|
| cyp52M1 deficient strain | 0.003 | 0 | 0 | 100 |
| cyp52M1::pGAPDH-WcSLI1 strain | 31.4 | 23.8 | 10.1 | 66.1 |
| cyp52M1::pGAPDH-ScSLI1 strain | 0.005 | 0 | 0 | 100 |
| cyp52M1::pGAPDH-PpSLI1 strain | 0.006 | 0 | 0 | 100 |

What is claimed is:

1. A method for producing a triacetylated phytosphingosine composition that comprises a higher total amount of C18, C19 and C20 triacetylated phytosphingosines than C18, C19 and C20 monoacetylated phytosphingosines, the method comprising
   culturing *Starmerella bombicola* into which a xenogeneic gene encoding a polypeptide having an activity to acetylate a sphingoid base has been introduced, wherein the polypeptide having an activity to acetylate a sphingoid base consists of a polypeptide selected from the following (a) to (c):
   (a) a polypeptide consisting of the amino acid sequence of SEQ ID NO:2,
   (b) a polypeptide consisting of an amino acid sequence that has a deletion, substitution or addition of one to ten amino acid residues in the amino acid sequence of SEQ ID NO:2, or
   (c) a polypeptide consisting of an amino acid sequence having a homology of 95% or more with the amino acid sequence of SEQ ID NO:2,
   wherein the culturing produces a composition that comprises at least one of:
   triacetylated phytosphingosine having a sphingoid base carbon chain length of 18 carbon atoms (C18);
   triacetylated phytosphingosine having a sphingoid base carbon chain length of 19 carbon atoms (C19); and
   triacetylated phytosphingosine having a sphingoid base carbon chain length of 20 carbon atoms (C20);
   wherein the total amount of the C18, C19 and C20 triacetylated phytosphingosines that is produced is greater than the total amount of C18, C19 and C20 monoacetylated phytosphingosines that is produced, and
   wherein the total amount of the C18, C19 and C20 triacetylated phytosphingosines that is produced is greater than the amount produced by culturing a control *Starmerella bombicola* into which the xenogeneic gene was not introduced.

2. The method according to claim 1, wherein the culturing produces a triacetylated phytosphingosine composition that comprises a triacetylated phytosphingosine having a sphingoid base carbon chain length of 20 carbon atoms (C20).

3. The method according to claim 1, wherein the culturing produces a triacetylated phytosphingosine composition that comprises a triacetylated phytosphingosine having a sphingoid base carbon chain length of 18 carbon atoms (C18).

4. The method according to claim 1, wherein the culturing is performed in a medium to which a pentadecanoic acid alkyl ester, a heptadecanoic acid alkyl ester or a nonadecanoic acid alkyl ester is added and a triacetylated phytosphingosine having an acetylated sphingoid base chain length of 19 carbon atoms (C19) is produced.

5. The method according to claim 1, wherein the culturing is performed in a medium to which an octadecanoic acid alkyl ester is added and a triacetylated phytosphingosine having an acetylated sphingoid base chain length of 20 carbon atoms (C20) is produced.

6. A *Starmerella bombicola* into which a xenogeneic gene encoding a polypeptide having an activity to acetylate a sphingoid base is introduced, wherein the polypeptide having an activity to acetylate a sphingoid base consists of an amino acid sequence selected from the following (a) to (c):
   (a) a polypeptide consisting of the amino acid sequence of SEQ ID NO:2,
   (b) a polypeptide consisting of an amino acid sequence that has a deletion, substitution or addition of one to ten amino acid residues in the amino acid sequence of SEQ ID NO:2, and
   (c) a polypeptide consisting of an amino acid sequence having a homology of 95% or more with the amino acid sequence of SEQ ID NO:2.

7. The method of claim 1, wherein the polypeptide is polypeptide (a), a polypeptide consisting of the amino acid sequence of SEQ ID NO:2.

8. The method of claim 1, wherein the polypeptide is polypeptide (c), a polypeptide consisting of an amino acid sequence having a homology of 95% or more with the amino acid sequence of SEQ ID NO:2.

9. The *Starmerella bombicola* of claim 6, wherein the polypeptide is polypeptide (a), a polypeptide consisting of the amino acid sequence of SEQ ID NO:2.

10. The method according to claim 1, wherein the culturing produces a triacetylated phytosphingosine composition that comprises a triacetylated phytosphingosine having a sphingoid base carbon chain length of 19 carbon atoms.

11. A method for producing a monoacetylated phytosphingosine composition that comprises a higher total amount of C19 and C20 monoacetylated phytosphingosines than C19 and C20 triacetylated phytosphingosines, the method comprising
    culturing *Starmerella bombicola* into which a xenogeneic gene encoding a polypeptide having an activity to acetylate a sphingoid base has been introduced, wherein the polypeptide having an activity to acetylate a sphingoid base consists of a polypeptide selected from the following (d) to (i):
    (d) a polypeptide consisting of the amino acid sequence of SEQ ID NO:4,
    (e) a polypeptide consisting of an amino acid sequence that has a deletion, substitution or addition of one to ten amino acid residues in the amino acid sequence of SEQ ID NO:4, (f) a polypeptide consisting of an amino acid sequence having a homology of 95% or more with the amino acid sequence of SEQ ID NO:4, (g) a polypeptide consisting of the amino acid sequence of SEQ ID NO:6, (h) a polypeptide consisting of an amino acid sequence that has a deletion, substitution or addition of one to ten amino acid residues in the amino acid sequence of SEQ ID NO:6, and (i) a polypeptide consisting of an amino acid sequence having a homology of 95% or more with the amino acid sequence of SEQ ID NO:6, wherein the culturing produces a monoacetylated phytosphingosine composition that comprises at least one of:

monoacetylated phytosphingosine having a sphingoid base carbon chain length of 19 carbon atoms (C19); and monoacetylated phytosphingosine having a sphingoid base carbon chain length of 20 carbon atoms (C20);

wherein the total amount of the C19 and C20 monoacetylated phytosphingosines that is produced is greater than the total amount of C19 and C20 triacetylated phytosphingosines that is produced, and wherein the total amount of the C19 and C20 monoacetylated phytosphingosines that is produced is greater than the amount produced by culturing a control *Starmerella bombicola* into which the xenogeneic gene was not introduced.

12. The method according to claim 11, wherein the culturing produces a monoacetylated phytosphingosine composition that comprises a monoacetylated phytosphingosine having a sphingoid base carbon chain length of 20 carbon atoms (C20).

13. The method according to claim 11, wherein the culturing produces a monoacetylated phytosphingosine composition that comprises a monoacetylated phytosphingosine having a sphingoid base carbon chain length of 19 carbon atoms (C19).

14. The method according to claim 11, wherein the culturing is performed in a medium to which a pentadecanoic acid alkyl ester, a heptadecanoic acid alkyl ester or a nonadecanoic acid alkyl ester is added and a monoacetylated phytosphingosine having an acetylated sphingoid base chain length of 19 carbon atoms (C19) is produced.

15. The method according to claim 11, wherein the culturing is performed in a medium to which an octadecanoic acid alkyl ester is added and a monoacetylated phytosphingosine having an acetylated sphingoid base chain length of 20 carbon atoms (C20) is produced.

16. The method of claim 11, wherein the polypeptide is polypeptide (d), a polypeptide consisting of the amino acid sequence of SEQ ID NO:4.

17. The method of claim 11, wherein the polypeptide is polypeptide (g), a polypeptide consisting of the amino acid sequence of SEQ ID NO:6.

18. The method of claim 11, wherein the polypeptide is polypeptide (f), a polypeptide consisting of an amino acid sequence having a homology of 95% or more with the amino acid sequence of SEQ ID NO:4.

19. The method of claim 11, wherein the polypeptide is polypeptide (i), a polypeptide consisting of an amino acid sequence having a homology of 95% or more with the amino acid sequence of SEQ ID NO:6.

20. A *Starmerella bombicola* into which a xenogeneic gene encoding a polypeptide having an activity to acetylate a sphingoid base is introduced, wherein the polypeptide having an activity to acetylate a sphingoid base consists of an amino acid sequence selected from the following (d) to (i):

(d) a polypeptide consisting of the amino acid sequence of SEQ ID NO:4, (e) a polypeptide consisting of an amino acid sequence that has a deletion, substitution or addition of one to ten amino acid residues in the amino acid sequence of SEQ ID NO:4, (f) a polypeptide consisting of an amino acid sequence having a homology of 95% or more with the amino acid sequence of SEQ ID NO:4, (g) a polypeptide consisting of the amino acid sequence of SEQ ID NO:6, (h) a polypeptide consisting of an amino acid sequence that has a deletion, substitution or addition of one to ten amino acid residues in the amino acid sequence of SEQ ID NO:6, and (i) a polypeptide consisting of an amino acid sequence having a homology of 95% or more with the amino acid sequence of SEQ ID NO:6.

21. The *Starmerella bombicola* of claim 20, wherein the polypeptide is polypeptide (d), a polypeptide consisting of the amino acid sequence of SEQ ID NO:4.

22. The *Starmerella bombicola* of claim 20, wherein the polypeptide is polypeptide (g), a polypeptide consisting of the amino acid sequence of SEQ ID NO:6.

* * * * *